US006309870B1

(12) United States Patent
Kondo et al.

(10) Patent No.: US 6,309,870 B1
(45) Date of Patent: Oct. 30, 2001

(54) PHYTASE AND GENE ENCODING SAID PHYTASE

(75) Inventors: Hidemasa Kondo; Hideharu Anazawa, both of Tokyo; Syunichi Kaneko, Aichi; Tadashi Nagashima, Aichi; Tatsuya Tange, Aichi, all of (JP)

(73) Assignees: Kyowa Nakko Kogyo Co., Ltd., Tokyo; Shin Nihon Chemical Co., Ltd., Anjo, both of (JP)

( * ) Notice: Subject to any disclaimer, the term of this patent is extended or adjusted under 35 U.S.C. 154(b) by 0 days.

(21) Appl. No.: 09/543,744

(22) Filed: Apr. 5, 2000

Related U.S. Application Data

(62) Division of application No. 09/155,855, filed as application No. PCT/JP97/01175 on Apr. 4, 1997, now Pat. No. 6,139,902.

(30) Foreign Application Priority Data

Apr. 5, 1996 (JP) .................................................. 8-084314

(51) Int. Cl.[7] .............................. C12N 9/16; C12N 1/20; C12N 1/14; C12N 15/00; C07H 21/04
(52) U.S. Cl. ................. 435/196; 435/252.3; 435/254.11; 435/254.3; 435/320.1; 536/23.2
(58) Field of Search ................................ 435/196, 252.3, 435/254.11, 254.3, 256.1, 320.1; 536/23.2

(56) References Cited

U.S. PATENT DOCUMENTS

| 5,436,156 | 7/1995 | Van Gorcom et al. | 435/252.3 |
| 5,780,292 | 7/1998 | Nevalainen et al. | 435/256.8 |

OTHER PUBLICATIONS

Hara et al. (1985) Agric. Biol. Chem 49, pp. 3539–3544.

*Primary Examiner*—Elizabeth Slobodyansky

(57) ABSTRACT

This invention relates to an inexpensive phytase with a low Km value for phytic acid, DNA coding for the phytase, recombinant DNA having the DNA introduced thereinto, a transformant carrying the recombinant DNA, a process for preparing a phytase by use of the transformant, and an animal feed comprising the phytase.

23 Claims, 5 Drawing Sheets

PHYTASE AND GENE ENCODING SAID PHYTASE

This application is a divisional application of U.S. Ser. No. 09/155,855, filed Oct. 5, 1998, now U.S. Pat. No. 6,139,902 which in turn is a 371 application of PCT/JP97/01175 filed Apr. 4, 1997.

TECHNICAL FIELD

The present invention relates to an inexpensive phytase with a low Michaelis constant (hereinafter abbreviated to Km) for phytic acid, which degrades phytic acid as an anti-trophic factor contained in feed, thereby improving the nutritive value of the feed and enabling an efficient utilization of phosphoric acid released by the degradation; and to a gene coding for the phytase.

BACKGROUND ART

Phosphorus is an essential element for all organisms. Plant-derived feeds used for the production of domestic animals contain phosphorus, 50 to 70% of which is present as phytic acid. Phytic acid is a major storage substance of phosphoric acid, existing in a large amount in plant seeds. However, phytic acid is excreted without digestion and absorption in the digestive organs in single-stomach animals such as pigs, chickens, etc. That is, phytic acid is a storage substance of phosphoric acid, but its phosphorus is not utilized at all. Accordingly, phosphoric acid is added to feed for single-stomach animals for the purpose of growth promotion.

Addition of phosphoric acid to the feed leads to an increase in the amount of phosphorus in excrement. In recent years, excrement from domestic animals increase considerably as the production of domestic animals increases more and more, whereby an environmental problem is now caused in the world. In particular, phosphorus contained in excrement is mentioned as a factor causing the phenomenon of nutrition enrichment in lakes and marshes, so the amount of phosphorus in excrement comes to be regulated, and there arises necessity for countermeasure.

In addition to the problem of excreted phosphorus, phytic acid chelates divalent metals important as a nutritive source, such as magnesium, calcium, zinc and iron, thereby making its absorption into animals difficult and reducing the nutritive value of feed. Accordingly, phytic acid is regarded as an anti-trophic factor.

From the foregoing, it has been examined to decrease the amount of phosphorus in excrement by treating the feed with a phytase known widely as an enzyme capable of hydrolyzing a salt of phytic acid into inositol and inorganic phosphoric acid in order to utilize phosphoric acid released from phytic acid in place of phosphoric acid conventionally added in feed, and it has also been examined to improve the nutritive value of the feed by decomposing phytic acid as an anti-trophic factor [U.S. Pat. No. 3,297,548 (1967); J. Nutrition, 101, 1289–1294 (1971)].

Known as phytase-producing microorganisms are bacteria such as *Bacillus subtilis* and Pseudomonas, yeasts such as *Saccharomyces cerevisiae*, and filamentous fungi such as *Aspergillus terreus*, *Aspergillus ficcum* and *Aspergillus awamori*.

For phytase derived from *Aspergillus ficcum*, its purification and biochemical properties are described in Preparative Biochem., 18, 443–458 (1988), and its gene and amino acid sequence are described in Gene, 127, 87–94 (1993).

For phytase derived from *Aspergillus awamori*, its nucleotide sequence and amino acid sequence are described in Gene, 133, 55–62 (1993).

Michaelis constants (Km) for phytases known so far are 0.57 mM for wheat bran-derived phytase [Agr. Biol. Chem., 26, 794–803 (1962)], 0.17 mM for rice bran-derived phytase [Agr. Biol. Chem., 53, 1475–1483 (1898)], 117 $\mu$M for maize (*Zea mays*)-derived phytase, 250 $\mu$M for *Aspergillus ficcum*-derived phytase (WO 91/05053), 330 $\mu$M for *Aspergillus oryzae*-derived phytase, 150 $\mu$M for *Bacillus subtilis*-derived phytase, 500 $\mu$M for *Bacillus natto*-derived phytase, and 130 $\mu$M for *Escherichia coli*-derived phytase.

To demonstrate the performance of the enzyme, the concentration of a substrate is necessary to be higher than Km, and if an enzyme with low Km and an enzyme with high Km have the same maximum reaction rate (Vmax), the enzyme with low Km does not decrease a reaction rate even at a lower substrate concentration as compared with the enzyme with high Km.

That is, when compared with the enzyme with high Km, the enzyme with low Km is advantageous in that a sufficient degradation rate can be achieved even at a lower substrate concentration, thereby minimizing the amount of the remaining substrate.

Accordingly, there is a demand for an inexpensive phytase with a low Km value for phytic acid, which phytase degrades phytic acid being an anti-trophic factor contained in feed, thereby improving the nutritive value of the feed and simultaneously achieving an efficient utilization of phosphoric acid released by the degradation.

DESCRIPTION OF THE INVENTION

The present invention relates to a phytase (hereinafter referred to as "novel phytase") having a Michaelis constant of 10 to 30 $\mu$M when using phytic acid as the substrate, DNA coding for the phytase, recombinant DNA having the DNA introduced thereinto, a transformant carrying the recombinant DNA, a process for preparing a phytase by use of the transformant, and an animal feed containing the phytase.

The present invention will be described in detail.

A specific example of the novel phytase of the present invention includes: a phytase with the following physicochemical properties:

(1) Km value: 10 to 30 $\mu$M;
(2) molecular weight (by SDS-PAGE): about 60 kDa after treatment with endoglycosidase H;
(3) optimum pH: pH 5.0 to 6.5;
(4) optimum temperature: 45 to 65° C. showing maximum activity;
(5) substrate specificity: acting on the substrates, phytic acid, p-nitrophenylphosphate, D-glucose 6-phosphate, fructose 6-phosphate, D-myo-inositol 1,4,5-triphosphate, glycerol phosphate, and adenosine triphosphate; and
(6) isoelectric focusing: pI 4.7 to 5.4.; or a phytase protein having the amino acid sequence shown in SEQ ID NO:1 or 2.

Furthermore, the present invention encompasses a novel phytase having an amino acid sequence (for example, shown in SEQ ID NO:3) in which a secretory signal sequence has been linked to the novel phytase described above.

The present invention further includes a phytase having an amino acid sequence comprising substitutions, deletions or additions of one or more amino acids relative to the amino acid sequence shown in SEQ ID No: 1, 2 or 3; having a homology of 40% or more to the amino acid sequence shown in SEQ ID NO:1, 2 or 3; and having a Michaelis constant (Km) of 10 to 30 μM when using phytic acid as the substrate. The phytase has preferably a homology of 60% or more, more preferably 80% or more.

The substitution, deletion or addition of amino acids can be carried out according to methods described in Nucleic Acids Research, 10, 6487 (1982), Proc. Natl. Acad. Sci., USA, 79, 6409 (1982), Proc. Natl. Acad. Sci., USA, 81, 5662 (1984), Science, 224, 1431 (1984), PCT WO85/00817 (1985), Nature, 316, 601 (1985), Gene, 34, 315 (1985), Nucleic Acids Research, 13, 4431 (1985), Current Protocols in Molecular Biology, chapter eight "Mutagenesis of Cloned DNA", John Wiley & Sons, Inc. (1989), etc.

The novel phytase can also be obtained from any microorganisms having the ability to produce it. Among them, preferable examples are microorganisms belonging to the genus Aspergillus and having the ability to produce the novel phytase. More preferable examples include *Aspergillus niger* strain SK57 (FERM BP-5473) or mutants or derived strains thereof. *Aspergillus niger* strain SK92 (FERM BP-5481) is included in mutants derived from *Aspergillus niger* strain SK57.

The gene (hereinafter referred to as "novel phytase gene") coding for the novel phytase of the present invention may be any gene coding for the novel phytase: for example, a gene coding for a phytase having the amino acid sequence shown in SEQ ID NO:1, 2 or 3; or a gene coding for a phytase which has an amino acid sequence where in the amino acid sequence shown in SEQ ID NO:1, 2 or 3, one or more amino acids have been substituted, deleted or added and which has a Michaelis constant (Km) of 10 to 30 μM when using phytic acid as the substrate. The gene may contain introns in the DNA sequence. Specifically, the gene of the present invention includes DNA shown in SEQ ID NO:4, or DNA shown in SEQ ID NO:5 containing introns in its sequence.

Further, the novel phytase gene of the present invention includes DNA capable of hybridizing under stringent conditions with the above-defined DNA, and of bringing about the corresponding phytase activity.

The term "DNA capable of hybridizing under stringent conditions" as described herein refers to DNA obtainable using colony hybridization, plaque hybridization or Southern blot hybridization wherein any DNA contained in the base sequence shown in SEQ ID NO:4 or 5 is used as a probe. A specific example thereof is DNA which can be identified by subjecting it to hybridization with a colony or plaque derived DNA-immobilized filter in the presence 0.7 to 1.0 M NaCl at 65° C. and then washing the filter at 65° C. with a 0.1 to 2×SSC solution (1×SSC solution is composed of 150 mM sodium chloride and 15 mM sodium citrate).

Hybridization can be effected according to methods described in Molecular Cloning, A Laboratory Manual, 2nd ed., Sambrook, Fritsch, Maniatis, Cold Spring Harbor Laboratory Press (1989)(hereinafter abbreviated to "Molecular Cloning, 2nd ed."). Specifically, the DNA capable of hybridizing includes DNA having a homology of 60% or more, preferably 80% or more, more preferably 95% or more to the base sequence of SEQ ID NO:4 or 5.

A DNA fragment containing the novel phytase gene can be obtained from any microorganisms having the ability to produce novel phytase. Although any microorganism having the ability to produce novel phytase can be used, preferable examples are microorganisms belonging to the genus Aspergillus and having the ability to produce novel phytase, more preferably *Aspergillus niger* strain SK57 or mutants or derived strains thereof. *Aspergillus niger* strain SK92 is included in mutants of *Aspergillus niger* strain SK57.

*Aspergillus niger* strain SK57 was deposited as FERM BP-5473 on Mar. 22, 1996 and *Aspergillus niger* strain SK92 as FERM BP-5481 on Mar. 12, 1996, respectively, with the National Institute of Bioscience and Human-Technology, Agency of Industrial Science and Technology, 1–3, Higashi 1-chome, Tsukuba-shi, Ibaraki-ken, 305 Japan.

Further, an animal feed comprising the novel phytase is included in the present invention.

Hereinafter, the method of obtaining the phytase gene derived from microorganisms having the ability to produce the novel phytase will be described.

Chromosomal DNA is prepared from microorganisms having the ability to produce the novel phytase by using a conventional DNA isolation method, forexample, thephenolmethod [Biochim. Biophys. Acta., 72, 619 (1963)]. The resulting chromosomal DNA is cleaved with suitable restriction enzymes, and these fragments cleaved with the restriction enzymes are introduced into vector DNA to construct a genomic DNA library from the microorganism. This DNA library is used to transform a host microorganism. The resulting transformants are selected for a transfornant containing the novel phytase gene through hybridization. A DNA containing the gene of interest can be obtained from the selected transformant.

A series of these procedures can follow in vitro recombination techniques known in the art (Molecular Cloning, 2nd ed.).

The vector DNA for constructing the genomic cDNA library of the microorganism having the ability to produce novel phytase may be any of phage vectors, plasmid vectors, etc. which are autonomously replicable in *E. coli* strain K12. Examples thereof are ZAP Express [Strategies, 5, 58 (1992); Stratagene], pBluescript II SK(+) [Nucleic Acids Research, 17, 9494 (1989), Stratagene], λzap II (Stratagene), λgt10, λgt11 [DNA Cloning, A Practical Approach, 1, 49 (1985)], Lambda BlueMid (Clonetech), λExCell (Pharmacia), pT7 T3 18U (Pharmacia), pcD2 [Mol. Cell. Biol., 3, 280 (1983)) and pUC18 [Gene, 33, 103 (1985)].

The host microorganism may be any microorganism belonging to the genus Escherichia. Examples thereof are *Escherichia coli* XL1-Blue MRF' [Strategies, 5, 81 (1992); Stratagene], *Escherichia coli* C600 [Genetics, 39, 440 (1954)], *Escherichia coli* Y1088 [Science, 222, 778 (1983)], *Escherichia coli* Y1090 [Science, 222, 778 (1983)], *Escherichia coli* NM522 [J. Mol. Biol., 166, 1 (1983)], *Escherichia coli* K802 [J. Mol. Biol., 16, 118 (1996)], *Escherichia coli* JM105 [Gene, 38, 275 (1985)], *Escherichia coli* JM109, *Escherichia coli* XL1-Blue, *Escherichia coli* XL2-Blue, *Escherichia coli* DH1, *Escherichia coli* MC1000, etc.

The transformant carrying the novel phytase gene can be selected by hybridization.

The probe useful in hybridization includes an oligonucleotide synthesized on the basis of a partial amino acid sequence determined for novel phytase. If another phytase gene has already been obtained from a class of microorganism closely related to the microorganism having the ability to produce novel phytase, the gene can be used in some case as the probe for the novel phytase gene. The gene which can be used in such case as the probe includes a phytase gene from *Aspergillus ficcum*.

The phytase gene from *Aspergillus ficcum* can be obtained by preparing its chromosomal DNA according to the above-described method and amplifying its phytase gene by polymerase chain reaction (PCR) with DNA primers which have been synthesized based on the DNA sequence of the phytase gene from *Aspergillus ficcum*.

The DNA primers can be synthesized using a conventional DNA synthesizer such as a DNA synthesizer (Shimadzu Seisakusho, Japan) utilizing the thiophosphite method, a DNA synthesizer model 392 (Perkin Elmer) or 380A DNA synthesizer (Applied Systems) utilizing the phosphoamidite method. Examples of the DNA primer synthesized in this manner include DNAs shown in SEQ ID NOS:6 and 7.

The DNA containing the novel phytase gene obtained from the transformant selected by hybridization is analyzed by the method such as the dideoxy method of Sanger et al. [Proc. Natl. Acad. Sci. USA, 74, 5463 (1977)], whereby the base sequence of the gene can be determined. The analysis of the base sequence can also be effected using an automatic base sequence analyzer such as SQ-5500 DNA sequencer (Hitachi) or 373A DNA sequencer [Perkin Elmer].

The thus determined nucleotide sequence of the novel phytase gene includes e.g. the nucleotide sequence of SEQ ID NO:4 or 5.

For expression in hosts, the novel phytase gene thus obtained may be expressed by the method described in Molecular Cloning, 2nd ed. or Current Protocols in Molecular Biology Supplements 1–34.

First, the DNA fragment containing the novel phytase gene is cleaved with restriction enzymes or DNase to form DNA fragments having a suitable size containing the novel phytase gene, then inserted into a region downstream of a promoter in an expression vector, followed by introducing the expression vector into which the DNA has been inserted, into a host compatible with the expression vector.

Any host can be used insofar as it can express the gene of interest. Examples thereof include prokaryotes belonging to the genera Escherichia, Serratia, Corynebacterium, Brevibacterium, Pseudomonas, Bacillus, Microbacterium, etc.; filamentous fungi belonging to the genera Aspergillus, Rhizopus, Trichodta, Neurospora, Mucor, Penicillium, etc.; yeasts belonging to the genera Kluyveromyces, Saccharomyces, Schizosaccharomyces, Trichosporon, Schwanniomyces, etc.; animal cells; and insect cells.

The expression vector used is one capable of autonomously replicating in the above host or capable of integrating into the chromosome, containing a promoter at a site enabling transcription of the novel phytase gene.

If prokaryotes such as bacteria are used as the host, the expression vector for novel phytase is preferably one capable of autonomously replicating in the microorganism and comprising a promoter, a ribosome-binding sequence, the novel phytase gene, and a transcription termination sequence. The vector may also contain a gene for regulating the promoter.

Expression vectors include e.g. pKK233-2 (Pharmacia), pSE280 (Invitrogen), pGEMEX-1 (Promega), pQE-8 (Qiagen), pKYP10 (JP-A-110600/1983), pKYP200 [Agric. Biol. Chem., 48, 669 (1984)], pLSA1 [Agric. Biol. Chem., 53, 277 (1989)], pGEL1 [Proc. Natl. Acad. Sci., USA, 82, 4306 (1985)], pBluescript (Stratagene), pTrs30 [prepared from *Eschericha coli* JM109/pTrS30 (FERM BP-5407)], pTrs32 [prepared from *Esherichia coli* JM109/pTrS32 (FERM BP-5408)], pGHA2 (*E. coli* containing pGHA2 has been deposited as *Escherichia coli* IGHA2 (FERM BP-400) with the National Institute of Bioscience and Human-Technology, Agency of Industrial Science and Technology, Japan; see JP-A-221091/1985], pGKA2 [*E. coli* containing pGKA2 has been deposited as *Escherichia coli* IGKA2 (FERM B-6798) with the National Institute of Bioscience and Human-Technology, Agency of Industrial Science and Technology, JP-A-221091/1985], pTerm2 (JP-A-22979/1991, USP 4686191, USP 4939094, USP 5160735), pGEX (Pharmacia), pET system (Novagen), and pSupex.

Any promoter can be used insofar as it can be expressed in a host such as *E. coli*. Examples thereof are promoters derived from *E. coli*, phage etc., such as trp promoter (Ptrp), lac promoter (Plac), $P_L$ promoter and $P_R$ promoter. Further, artificially modified promoters are usable, whose examples are a Ptrp×2 promoter (having 2 Ptrp promoters in series), tac promoter, T7 promoter, PletI promoter, etc.

The ribosome-binding sequence used is preferably a plasmid in which the distance between a Shine-Dalgarno sequence and an initiation codon is suitably regulated (e.g. distance of 6 to 18 bases).

Although any gene coding for the novel phytase can be used as the novel phytase gene, its nucleotides are preferably replaced such that the DNA sequence of the gene is composed of optimum codons for expression in host microorganisms.

Although a transcription termination sequence is not necessarily required for expression of the gene of the present invention, it is preferable to locate the transcription termination sequence at a site just downstream of the structural gene.

The host includes microorganisms belonging to the genera Escherichia, Serratia, Corynebacterinm, Brevibacterium, Pseudomonas, Bacillus, etc., for example, *Eschericha coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Bacillus subtilis*, *Bacillus amyloliquefacines*, *Brevibacterium immariophilum* ATCC14068, *Brevibacterium saccharolyticum* ATCC14066, *Brevibacterium flavum* ATCC14067, *Brevibacterium lactofermentum* ATCC13869, *Corynebacterium glutamicum* ATCC13032, *Corynebacterium acetoacidophilum* ATCC13870, and *Microbacterium ammoniaphilum* ATCC15354.

If filamentous fungi are used as the host, examples of expression vectors are p3SR2 [Gene, 26, 205–221 (1983)], pKBY2 [Proc. Natl. Acad. Sci. USA, 82, 834–838 (1985)], pSal23 [Agric. Biol. Chem., 51, 2549–2555 (1987)], pSTA14 [Mol. Gen. Genet., 218, 99–104 (1989)], pDJB2 [Gene, 36, 321–331 (1989)], and pLeu4 [Biosci. Biotech. Biochem., 56, 1503–1504 (1992)].

Any promoter can be used insofar as it allows expression to induce in filamentous fungi as the host. Examples are a promoter induced strongly by starch or cellulose, e.g. a promoter for glucoamylase or α-amylase from the genus Aspergillus or cellulase (cellobiohydrase) from the genus Trichoderma, a promoter for enzymes in the glycolytic pathway, such as phosphoglycerate kinase (pgk) and glyceryaldehyde 3-phosphate dehydrogenase (gpd), etc.

Although any gene coding for the novel phytase can be used as the novel phytase gene, a preferable example is a gene coding for a protein having an amino acid sequence to which a peptide having a secretory signal sequence at an N-terminal amino acid of the novel phytase has been linked to permit secretion of the novel phytase out of the microorganism cell. The peptide having a secretory signal sequence includes e.g. a peptide having a secretory signal sequence for glucoamylase or α-amylase from the genus Aspergillus, or a peptide having the 1–24 amino acid sequence shown in SEQ ID NO:2.

The host includes *Aspergillus niger* SK57, *Aspergillus oryzae* M-2-3 [Agric. Biol. Chem., 51, 2549–2555 (1987)]; *Aspergillus ficcum* NRRL3135, *Aspergillus awamori* NRRL3112, *Aspergillus nidulans* IFO4340, *Trichoderma reesei* Rut-C-30 [Appl. Microbiol. Biotechnol., 20, 46–53

(1984)], *Rhizopus niveus* M-37 [Biosci. Biotech. Biochem., 56, 1503–1504 (1992)], etc.

Transformation of filamentous fungi can be performed according to the method of Gomi et al. [Agric. Biol. Chem., 51, 2549 (1987)] or the like.

If yeasts are used as the host, expression vectors such as YEp 13 (ATCC37115), YEp 24 (ATCC37051) and YCp 50 (ATCC37419) can be enumerated.

Any promoter capable of expressing in yeast hosts can be used as the promoter. Examples thereof include promoters for genes of hexokinase and the like in the glycolytic pathway, and promoters such as gal 1 promoter, gal 10 promoter, heat shock protein promoter, MFα1 promoter and CUP 1 promoter.

Examples of the host are *Saccharomyces cerevisiae, Schizosaccharomyces pombe, Kluyveromyces lactis, Trichosporon pullulans, Schwanniomyces alluvius*, etc.

Introduction of the recombinant vector can be carried out by any method of introducing DNA into yeasts, such as electroporation method [Methods, Enzymol., 194, 182 (1990)], spheroplast method [Proc. Natl. Aad. Sci. USA, 84, 1929 (1978)], lithium acetate method [J. Bacteriol., 153, 163 (1983)] and the like.

If animal cells are used as the host, expression vectors used are, e.g., pAGE107 [JP-A-22979/1991; Cytotechnology, 3, 133 (1990)], pAS3-3 (JP-A-227075/1990), pCDM8 [Nature, 329, 840 (1987)], pcDNAI/Amp (Invitrogen), pREP4 (Invitrogen), pAGE103 [J. Biochem., 101, 1307 (1987)], and pAGE210.

Any promoter which allows expression to induce in animal cells can be used. Examples thereof are a promoter for an IE (immediate early) gene in cytomegalovirus (human CMV), an SV40 early promoter, and a promoter for metallothionein. Also, an enhancer for the IE gene from human CMV may be used together with the promoter.

The host cells include Namalwa cell that is a human cell, COS cell that is a monkey cell, CHO cell that is a Chinese hamster cell, HBT5637 (JP-A-299/1988), etc.

Any method capable of introducing DNA into animal cells can be used: for example, electroporation method [Cytotechnology, 3, 133 (1990)], calcium phosphate method (JP-A-227075/1990), lipofection method [Proc. Natl. Acad. Sci. USA, 84, 7413 (1987)], etc.

Preparation and culture of the transformant can be conducted according to the methods described in JP-A-227075/1990 or JP-A-257891/1990.

If an insect cell is used as the host, a gene for the protein of interest can be expressed by the methods described in e.g. Baculovirus Expression Vectors, A Laboratory Manual; Current Protocols in Molecular Biology Supplements 1–34; and Bio/Technology, 6, 47 (1988).

That is, the vector into which the recombinant gene has been introduced is introduced together with baculovirus into an insect cell so that a recombinant virus is obtained in the supernatant of the cultured insect cell. Then, insect cells are infected with the recombinant virus whereby the protein can be expressed.

The gene-introducing vector used in this method includes e.g. pLV1392, pVL1393, and pBlueBacIII (which all are products of Invitrogen).

As the baculovirus, it is possible to employ e.g. Autographa californica nuclear polyhedrosis virus, which is a virus infecting certain moth insects.

As the insect cells, it is possible to employ ovary cells Sf9 and Sf21 from *Spodoptera frugiperda* [Baculovirus Expression Vectors, A Laboratory Manual, W. H. Freeman and Company, New York (1992)], High 5 (Invitrogen) which is an ovary cell from *Trichoplusia ni*, etc.

For co-introduction of both the vector having the recombinant gene and the baculovirus into an insect cell to prepare a recombinant virus, the calcium phosphate method (JP-A-227075/1990) or lipofection method [Proc. Natl. Acad. Sci. USA, 84, 7413 (1987)] may be used.

Expression of the gene may be performed in a secretion manner or as expression of a fusion protein in accordance with the methods described in Molecular Cloning, 2nd ed., in addition to direct expression.

In the case of expression in filamentous fungi, yeasts, animal cells or insect cells, polypeptides having saccharide or carbohydrate chains can be obtained.

Besides the above-described transformants, a microorganism having the ability to produce the novel phytase or its mutants having more improved ability to produce the novel phytase can be used to produce the novel phytase.

The mutant having the improved productivity of the novel phytase can be obtained through usual mutagenesis.

For preparation of the novel phytase, the microorganism having the ability to produce the novel phytase, mutants derived from the microorganism, or transformants carrying the recombinant DNA having the novel phytase gene integrated therein can be cultured by a conventional culture method to produce and accumulate the novel phytase, followed by recovering of the novel phytase from the culture. The microorganisms, mutants, and transformants used for producing the novel phytase are hereinafter referred to as novel phytase-producing organism.

If the novel phytase-producing organism is a prokaryote such as *E. coli* or a eukaryote such as filamentous fungous or yeast, the medium for culturing these organisms may be natural or synthetic insofar as the medium contains a carbon source, a nitrogen source, inorganic salts, and so on, which can be assimilated by the organisms and in which the transformants can be efficiently cultured.

Any carbon source can be used insofar as it can be assimilated by the microorganisms: for example, hydrocarbons such as glucose, fructose, sucrose, molasses containing them, starch, and starch hydrolysates; organic acids such as acetic acid and propionic acid; and alcohols such as methanol, ethanol and propanol.

Used as the nitrogen source are: ammonia; ammonium salts of inorganic or organic acids, such as ammonium chloride, ammonium sulfate, ammonium acetate and ammonium phosphate; and other nitrogenous compounds; peptone; meat extract (broth); yeast extract; corn steep liquor; casein hydrolysates; soybean cake and hydrolysates thereof; and a variety of fermentation microorganisms and digested materials thereof.

The inorganic matter used include monopotassium phosphate, dipotassium phosphate, magnesium phosphate, magnesium sulfate, sodium chloride, ferrous sulfate, manganese sulfate, copper sulfate, calcium carbonate, etc.

For culture of filamentous fungi, a medium with wheat bran, rice bran etc. as carbon, nitrogen and inorganic sources supplemented with suitable salts can also be used.

Culture is conducted under aerobic conditions using shake culture or submerged shake culture under aeration. The culture temperature is preferably 15 to 40° C., and the culture time is usually 16 to 96 hours. During culture, pH is kept at 3.0 to 9.0, and in culture of filamentous fungi, pH is kept preferably at 3.0 to 6.5. pH is adjusted with an inorganic or organic acid, an alkaline solution, urea, calcium carbonate, ammonia or the like.

During culture, an antibiotic such as ampicillin or tetracycline may optionally be added to the medium.

If a microorganism transformed with an expression vector having an inducible promoter as the promoter is cultured, its inducer may optionally be added to the medium. For example, isopropyl-β-D-thiogalactopyranoside (IPTG) or the like may be added to the medium for culture of a microorganism transformed with an expression vector having a lac promoter, and indoleacrylic acid (IAA) or the like may be added to the medium for culture of a microorganism transformed with an expression vector having a trp promoter.

If a filamentous fungus is cultured in a medium containing a solid component such as wheat bran, the filamentous fungus is inoculated and then well mixed with the solid component until they become uniform, after which the mixture is spread thinly on a number of aluminum or stainless steel trays, put in a cellar, and cultured under the control of temperature, humidity and aeration. More specifically, the fungus is subjected to stationary culture at 25 to 35° C. for 3 to 10 days under 100% humidity in a culture chamber.

If the novel phytase-producing organism is an animal cell, the medium used for culturing the cell is a generally used medium such as RPMI1640 medium, Eagle's MEM medium, or a medium supplemented with fetal calf serum or the like to said medium.

Culture may be conducted in the presence of 5% $CO_2$. The culture temperature is preferably 35 to 37° C., and the culture time is usually 3 to 7 days.

During culture, an antibiotic such as kanamycin or penicillin may optionally be added to the medium.

The medium for culture of the transformant prepared from an insect host cell may be a normal medium such as TNM-FH medium (Pharmingen), Sf-900 II SFM medium (Gibco BRL), and ExCell 400 and ExCell 405 [both, JRH Biosciences].

The culture temperature is preferably 25 to 30° C., and the culture time is usually 1 to 4 days.

During culture, an antibiotic such as gentamicin may optionally be added to the medium.

For isolation and purification of the novel phytase from a culture of the novel phytase-producing organism, the conventional isolation/purification of enzymes can be used.

For example, if the novel phytase is accumulated in a soluble form in cells of the novel phytase-producing organism, the cells are collected from the culture by centrifugation, then washed with an aqueous buffer and disrupted by ultrasonication using a French press, manntongaurin homogenizer, dynomill or the like, thereby giving a cell-free extract. The supernatant is obtained by centrifuging the cell-free extract and then subjected to the conventional isolation/purification of enzymes: namely, solvent extraction, salting-out with ammonium sulfate, desalting precipitation with organic solvent, anion-exchange chromatography on resin such as diethylaminoethyl (DEAE)-Sepharose or DIAION HPA-75 (Mitsubishi Corporation), anion-exchange chromatography on resin such as S-Sepharose FF (Pharmacia), hydrophobic chromatography on resin such as butyl Sepharose or phenyl Sepharose, gel filtration using molecular sieve, affinity chromatography, chromatofocusing, and electrophoresis such as isoelectric focusing, which means can be used singly or in combination, whereby a purified preparation can be obtained.

If the novel phytase is expressed in an insoluble form within cells, then, the cells are similarly recovered, disrupted and centrifuged to give a precipitated fraction from which the novel phytase is then recovered, and the insoluble novel phytase is solubilized with a detergent for polypeptide. The resultant liquid is then diluted or dialyzed to the degree that the detergent is not contained or does not cause denaturation of the polypeptide, whereby the novel phytase is reconstituted in the normal conformation. And a purified preparation can be obtained by the isolation/purification as described above.

If the novel phytase is secreted out of cells, the culture is centrifuged to give a soluble fraction. If ingredients in the medium contain a solid component such as wheat bran, the novel phytase can be extracted with warm water or the like and subjected to centrifugation to give a soluble fraction. From the soluble fraction, a purified preparation of the novel phytase can be obtained in the same way for isolation and purification from the cell-free extract as described above.

The activity of the novel phytase can be determined according to the standard assay method described below.

0.5 ml of 0.2 M acetate buffer, pH 5.5 (sodium acetate) containing 2.5 mM sodium phytate (Sigma) is maintained at 37° C. for 5 minutes, and 0.5 ml of an enzyme solution is added to initiate the reaction. After maintained at 37° C. for 10 minutes, 2 ml of a stop solution of enzyme reaction (i.e., mixture of 1:1:2 10 mM ammoniummolybdate, 5 N sulfuric acid and acetone) is added to stop the reaction, and 0.1 ml of 1 M citric acid is further added and mixed. The absorbance of this solution is determined at 380 nm on a spectrophotometer (Hitachi U-2000). One unit of phytase activity is defined as the amount of enzyme allowing to release 1 $\mu$mol inorganic phosphorus for 1 minute at pH 5.5 at 37° C.

The Km value of the novel phytase can be determined by the Lineweaver-Burk plot in which the activity of the novel phytase, as determined by the standard assay, is plotted at varying concentrations of the substrate.

The novel phytase of the present invention can be utilized in various processes required for converting a salt of phytic acid into inositol and inorganic phosphoric acid.

For example, the present enzyme can be used in animal feeds, soybean processing, liquid feeds for pigs and poultry, and production of inositol or inositol monophosphate from salts of phytic acid.

An example of such animal feeds is as follows:

The novel phytase of the present invention is mixed with a carrier material such as wheat chaff and dried in a spray tower or a fluidized bed. After drying, an osmotic pressure stabilizer such as sorbitol, and a preservative, such as benzoic acid, are further added to give an animal feed. The amount of the novel phytase in the animal feed is 10 to 5000 U, preferably 100 to 1000 U per kg of the animal feed.

BEST MODES FOR CARRYING OUT THE INVENTION

Example 1

Figure 1:
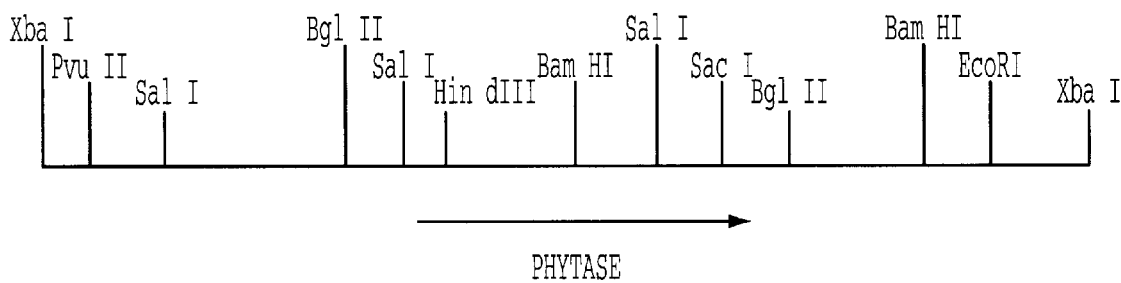
FIG. 1 shows a restriction enzyme map of a phytase gene derived from *Aspergillus niger* SK57, wherein the arrow indicates a phytase-coding region.

Preparation of Chromosomal DNA Coding for Novel Phytase

1. Preparation of *Aspergillus niger* SK57:

One hundred ml of a malt extract medium (2% malt extract, 2% glucose, 0.1% peptone) was put in a 500-ml Erlenmeyer flask with baffle, sealed with a silicon sponge stopper and sterilized at 120° C. for 20 minutes.

The strain SK57 was inoculated into the medium and cultured at 28° C. for 7 days under shaking.

The culture was filtered through a sterilized glass filter to yield 0.5 g of the strain SK57.

2. Isolation and purification of total DNA from the microorganism:

The strain SK57 obtained in Example 1-1 was placed between paper towels and pressed for dehydration. The microorganism was then put in a mortal cooled at −80° C., frozen by pouring liquid nitrogen, and finely disrupted with a pestle cooled at −80° C.

The finely disrupted microorganismwas put in a centrifugation tube, and 0.2 ml of TE buffer [10 mM Tris-HCl (pH 8.0), 1 mM EDTA] was added thereto, and suspended. The microorganism was lyzed by adding 0.2 ml of a lysis solution [2% SDS, 0.1 M NaCl, 10 mM EDTA, 50 mM Tris-HCl (pH 7.0)] to the suspension. The lysate was centrifuged at 15,000 r.p.m. (18,500×g) at 4° C. for 10 minutes, and the resulting supernatant was recovered in a new centrifugation tube.

Phenol solution (i.e., mixture of 25:24:1 phenol, chloroform and isoamyl alcohol) 0.4 ml was added to the supernatant which was then gently stirred and centrifuged at 15,000 r.p.m. (18,500×g) at 4° C. for 10 minutes to recover the supernatant in a new centrifugation tube. This procedure was repeated 3 times and the supernatant was recovered in another tube.

Cold ethanol 1 ml was added to the supernatant, then cooled at −80° C. for 10 minutes and centrifuged at 15,000 r.p.m. (18,500×g) at 4° C. for 10 minutes, thereby recovering a precipitate (DNA).

The precipitate was dried under vacuum and then dissolved in 0.5 ml of TE buffer.

Five µl of RNase A (10 mg/ml) was added to the solution and held at 37° C. for 30 minutes.

Phenol solution 0.5 ml was added to the above treated solution, and the mixture was gently stirred and centrifuged at 15,000 r.p.m. (18,500×g) for 10 minutes to recover the supernatant in a new centrifugation tube. This procedure was repeated twice, and the supernatant was recovered in a new centrifugation tube.

Chloroform solution (i.e., mixture of 24:1 chloroform and isoamyl alcohol) 0.5 ml was added to the above supernatant which was then centrifuged at 15,000 r.p.m. (18,500×g) at 4° C. for 10 minutes to recover a precipitate (DNA) in a new centrifugation tube.

Fifty µl of NaCl and 1 ml of cold ethanol were added to the supernatant which was then cooled at −80° C. for 10 minutes and centrifuged at 15,000 r.p.m. (18,500×g) at 4° C. for 10 minutes, thereby recovering a precipitate (DNA). The precipitate was further washed with 0.5 ml of 70% cold ethanol and centrifuged at 15,000 r.p.m. (18,500×g) at 4° C. for 10 minutes to recover a precipitate (DNA). After drying of the precipitate under vacuum, about 5 µg of purified genomic DNA was obtained.

3. Preparation of a probe:

Cloning of phytase from *Aspergillus niger* SK57 was examined using a gene from *Aspergillus ficcum* NRRL3135 [available from Northern Regional Research Center, United State Department of Agriculture Peoria, Ill. U.S.A. (NRRL)] as a probe.

Total DNA from the strain NRRL3135 was prepared by the methods described in Examples 1-1 and 1-2.

To amplify a phytase structural gene from NRRL3135, sense and antisense primers shown in SEQ ID NOS:6 and 7, respectively, were synthesized on 380A DNA synthesizer (Applied Biosystems). The phytase structural gene was amplified by PCR using 100 µl of a mixture containing the sense primer, the antisense primer and the genomic DNA from NRRL3135. PCR was conducted through the reaction steps: 92° C., 1 minute; 45° C., 2 minutes; and 72° C., 3 minutes per cycle; with 25 cycles in total.

After pUC118 was cleaved with the restriction enzyme Eco RI, a fragment of the PCR-amplified phytase structural gene which has been treated with Eco RI was inserted into the Eco RI cleavage site of pUC118 by use of the ligation kit (manufactured by Takara Shuzo, Japan).

The plasmid having the phytase structural gene fragment inserted therein was used to transform *E. coli* JM109 (Takara Shuzo).

The transformant *E. coli* was cultured at 37° C. for one day in LB medium (1% trypton, 0.5% yeast extract, 1% sodium chloride) containing 50 µg/ml ampicillin Na.

The plasmid was extracted from the cell culture and then digested with Eco RI to recover a 1.7-kb DNA fragment.

This 1.7-kb DNA fragment was used as a probe.

4. Southern hybridization:

Twelve U of restriction enzyme Xba I (Takara Shuzo) was added to 20 µg of the genomic DNA from the strain SK57, followed by reaction at 37° C. for 12 hours to cleave the DNA. This DNA was subjected to agarose gel electrophoresis. Southern hybridization with the probe obtained in Example 1-3 was conducted using ECL kit (Amersham) according to instructions attached to the kit.

After agarose gel electrophoresis, the DNA was capillary-blotted onto a Hybond-N$^+$ membrane (Amersham) in 0.4 N sodium hydroxide solution, and the membrane was air-dried. The membrane was immersed at 42° C. for 1 hour in 10 ml hybridization buffer [containing 0.5 M NaCl and 5% blocking reagent] of the ECL direct nucleic acid labeling and detection systems (Amersham), and 30 µl of a probe solution µwhich was prepared by adding 7 µl of sterilized water to 3 µl of the probe obtained in Example 1-3, keeping at 95° C. for 5 minutes, leaving on ice for 5 minutes, adding 10 µl of a labeling solution and 10 µl of glutaraldehyde solution, and keeping the resultant mixture at 37° C. for 10 minutes] was added to the hybridization buffer in which the blotting membrane has been immersed, followed by overnight shaking at 42° C.

The membrane was washed with 100 ml of a primary washing solution [6 M urea, 0.4% SDS, 0.5×SSC (1×SSC: 150 mM sodium chloride and 15 mM sodium citrate)] at 42° C. for 20 minutes. After washing, the membrane was washed with 100 ml of a secondary washing solution [0.4% SDS, 0.5×SSC] at 55° C. for 10 minutes, and this washing procedure was repeated. After washing, the membrane was washed with 100 ml of 2×SSC at room temperature for 5 minutes, and this washing procedure was conducted again.

The washed membrane was air-dried for 1 minute, immersed in 7 ml of a detection reagent for 1 minute, and rapidly wrapped in a Saran® wrap. The membrane was then set up into an X-ray film cassette and exposed to X-ray film (Fuji Film, Japan) at room temperature for 5 minutes.

A DNA fragment hybridizing strongly with the probe was detected at about 4.6 kb.

5. Preparation of chromosomal DNA library from *Aspergillus niger* SK57:

Restriction enzyme Xba I 12 U was added to 10 μg of the genomic DNA from the strain SK57, followed by reaction at 37° C. for 12 hours to cleave the DNA which was subsequently subjected to 0.8% agarose gel electrophoresis. After electrophoresis, about 4.6-kb DNA fragment was excised from the gel, from which 100 ng of the around 4.6-kb DNA fragment was obtained using Geneclean® (BIO 101).

Separately, 12 U of Xba I was added to 200 ng of the *E. coli* vector pUC118 (Takara Shuzo) followed by reaction at 37° C. for 1 hour to cleave pUC118.

One U of alkaline phosphatase was added to the thus treated solution. After 30-min reaction at 37° C., 20 μl of the phenol-treating solution was added to the reaction mixture, gently stirred, and centrifuged at 15,000 r.p.m. (18,500×g) at 4° C. for 10 minutes. The supernatant was then recovered in a new centrifugation tube. This procedure was repeated twice, and the supernatant was recovered in a new centrifugation tube.

Two μl of 3 M sodium acetate and 50 μl of cold ethanol were added to the supernatant which was then cooled at −80° C. for 10 minutes and centrifuged at 15,000 r.p.m. (18,500× g) at 4° C. for 10 minutes to recover a precipitate.

The precipitate was dried under vacuum and dissolved in 10 μl of TE buffer to obtain the cleaved fragment.

The about 4.6-kb DNA fragment prepared above was inserted into the cleavage site of the cleaved fragment by use of T4 ligase (Takara Shuzo), whereby the plasmid into which the chromosomal DNA fragment from *Aspergillus niger* SK57 has been introduced was yielded.

This plasmid was transformed into *E. coli* JM109 (Takara Shuzo) in a conventional manner.

The transformed *E. coli* was cultured at 37° C. for 1 day in LB medium containing 50 μg/ml ampicillin Na. To prepare a replica, the transformant was further cultured at 37° C. for 1 day in LB-agar medium (prepared by adding 2% agar to LB medium) containing 50 μg/ml ampicillin Na. The colonies grown thereon were used as a chromosomal DNA library from SK57.

6. Isolation of colonies having DNA of interest from the chromosomal DNA library:

To isolate colonies having the novel phytase gene from the library prepared in Example 1-5, the colonies were transferred from the library to a membrane filter and subjected to colony hybridization with the probe obtained in Example 1-3 by use of the ECL kit (Amersham). Several thousand colonies were subjected to hybridization to isolate positive colonies.

7. Preparation of a restriction enzyme map and sequencing:

A plasmid was extracted in a usual manner from the positive colonies obtained in Example 1-6. This plasmid was named pANPHY1. Plasmid pANPHY1 was digested with various restriction enzymes and subjected to agarose gel electrophoresis, and a restriction enzyme map of an Xba I-treated insert derived from the SK57 chromosomal DNA was made besed on the length of the fragments (FIG. 1). The insert had 4.6 kb in size.

Figure 2:
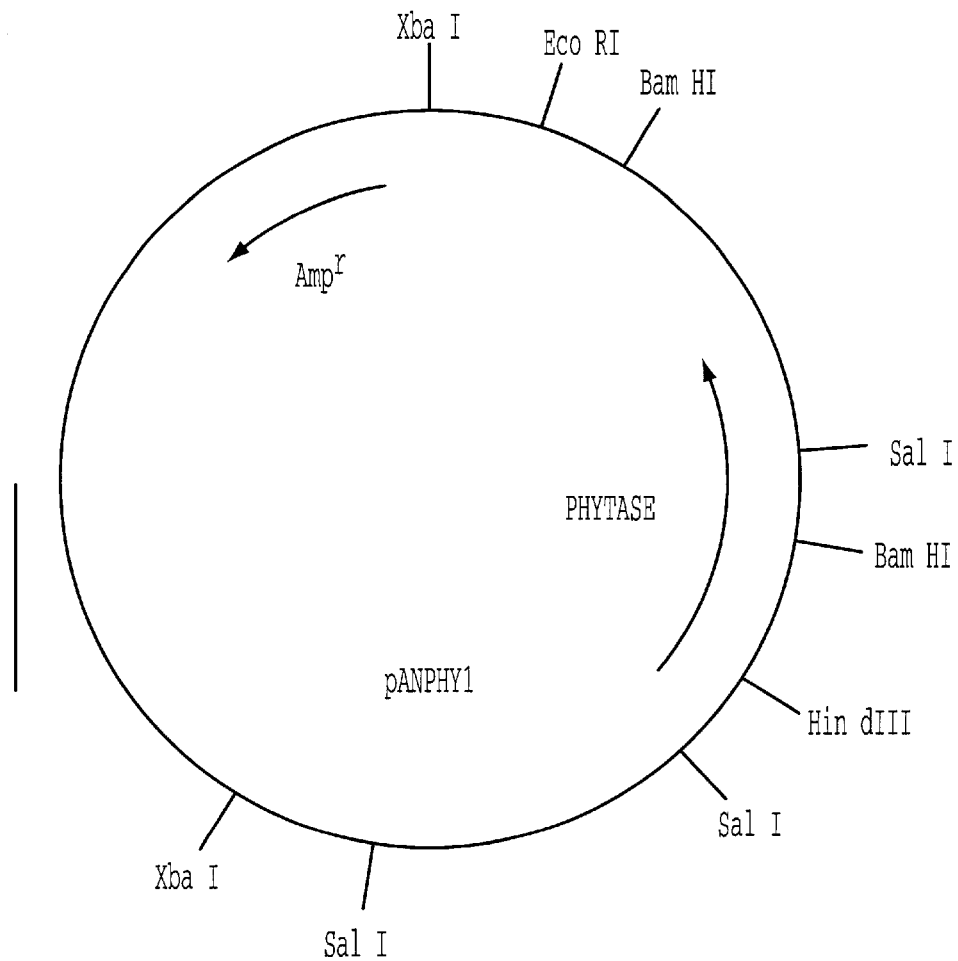
FIG. 2 shows a restriction enzyme map of the plasmid pANPHY1, wherein "Phytase" indicates a novel phytase gene, "Amp"" indicates an ampicillin-resistant gene from pUC118, and the arrow indicates the direction of transcription and translation of the gene.

Plasmid pANPHY1 was cleaved with various restriction enzymes, separated by agarose gel electrophoresis, and blotted onto a nylon membrane filter. Southern hybridization with the probe obtained in Example 1-3 was performed using the ECL kit. The site of hybridization with the probe was nearly in the middle of the insert. The restriction enzyme map of pANPHY1 and the coding region of novel phytase are shown in FIG. 2.

The whole nucleotide sequence of the novel phytase gene inserted into pANPHY1 was determined by the di-deoxy chain termination method. The nucleotide sequence is shown in SEQ ID NO:4.

Example 2
Analysis of Introns in DNA Coding for Novel Phytase

Intron regions in the chromosomal DNA coding for novel phytase obtained in Example 1 were analyzed by obtaining phytase cDNA from *Aspergillus niger* SK57 in the following manner.

1. Culture of *Aspergillus niger* SK57:

The medium was based on Czapek-Dox, containing 0.05% magnesium sulfate, 0.01% ferrous sulfate, 0.05% potassium chloride, 0.2% sodium nitrate, 1% glucose and 0.1% corn steep liquor (Sanei Toka, Japan) in 50 mM MES buffer. It was aliquoted in 500-ml flasks with baffle in an amount of 100 ml per flask, followed by sterilization in an autoclave (120° C., 20 minutes). After sterilization, the strain SK-5 was inoculated in an amount of a platinum loop from slants into the medium and cultured under shaking at 28° C. at 200 r.p.m. for 5 days, and then the microorganism was harvested on a glass filter under suction and rapidly frozen in liquid nitrogen for inhibition of RNase activity. It was stored at −80° C. until use.

2. Extraction of RNA:

One g of the frozen microorganism obtained in Example 1-1 was rapidly ground while pouring liquid nitrogen, and the resulting powder was added to 10 ml of the extraction liquid ISOGEN (Nippon Gene) at 50° C. and vigorously stirred for 30 seconds.

The solution was kept at 50° C. for 10 minutes and then aliquoted into Eppendorf tubes in an amount of 1 ml per tube.

Chloroform 200 μl was added to each aliquot, then shaken, and centrifuged at 15,000 r.p.m. (18,500×g) at 4° C. for 15 minutes, and the aqueous phase of the upper layer was recovered.

500 μl of 4 M lithium chloride was added to the aqueous phase, then mixed, left at −80° C. for 1 hour, and centrifuged at 15,000 r.p.m. at 4° C. for 15 minutes. The resulting precipitate was dissolved in 0.4 ml of RNase-free sterilized water (hereinafter abbreviated to RNase-free water).

Isopropyl alcohol 0.4 ml was added to the solution, and the mixture was left at 4° C. for 30 minutes and centrifuged again at 15,000 r.p.m. at 4° C. for 15.0 minutes to give a precipitate.

The precipitate was washed with 75% ethanol, then suitably dried in a vacuum centrifuge and dissolved in 0.4 ml of RNase-free water.

One ml of ethanol was added to the solution which was then centrifuged to give a precipitate again.

The precipitate was washed with 75% ethanol and dissolved in RNase-free water in a total volume of 0.4 ml. This was used as an RNA sample.

3. Amplification of phytase cDNA by RT-PCR:

The phytase CDNA was amplified using RT-PCR kit (Toyobo).

(1) Reverse transcription reaction

About 1 μg of the RNA sample obtained in Example 2-2 was put in an Eppendorf tube, and RNase-free water was added thereto to give 10 μl of the solution.

Four μl of 5×RTase buffer, 1 μl of random primer, 1 μl of RNase inhibitor and 2 μl of RTase, which were contained in the RT-PCR kit (Toyobo), were added to the above-prepared solution, followed by reactions at 30° C. for 10 minutes, at 42° C. for 20 minutes, at 99° C. for 5 minutes, and then at 4° C. for 5 minutes in PJ2000 thermal cycler (Perkin Elmer).

(2) PCR

Ten μl of Plus buffer, 68 μl of sterilized water, 0.5 μl of sense primer, 0.5 μl of antisense primer, and 1 μl of rTaq DNA polymerase, which were contained in the RT-PCR kit (Toyobo), were added to 20 μl of the reaction sample obtained in Example 2-1 to give 100 μl of the solution. The amplification of the cDNA for phytase was performed at 94° C. for 30 seconds, at 60° C. for 30 seconds, and then at 72° C. for 90 seconds per cycle, with 35 cycles in total.

After reaction, 10 μl of a mixture of chloroform and isoamyl alcohol (24:1) was added to the reaction mixture, stirred and then centrifuged at 15,000 r.p.m. for 5 minutes to recover the supernatant as a cDNA sample.

The cDNA sample was used for analysis of the cDNA and, as a result, one intron (positions 44 to 155) was found in the base sequence shown in SEQ ID NO: 5. This sequence coded for the amino acid sequence shown in SEQ ID NO: 3. From the amino acid sequence (SEQ ID NO:1) of the purified novel phytase protein described below, it was found that the amino acids from the N-terminus to the position 24 were corresponding to a secretory signal peptide.

Example 3
Preparation of Transformants Expressing Novel Phytase

Transformants expressing novel phytase were obtained from *Aspergillus niger* SK57, *Aspergillus nidulans* MD-4 and *Aspergillus oryzae* M-23 as hosts.

The host strain (*Aspergillus niger* SK57, *Aspergillus nidulans* MD-4 or *Aspergillus oryzae* M-23) was cultured at 30° C. for 2 to 3 days in DPY medium (2% dextrin, 1% peptone, 0.5% yeast extract, 0.5% $KH_2PO_4$, 0.05% $MgSO_4.7H_2O$, pH 5.5) under shaking. The grown microorganism was harvested using the 3G1 glass filter and washed with sterilized water.

The washed microorganism was added to 10 ml of protoplast-preparing solution [5 mg/ml Novozyme 234, 5 mg/ml cellulase R-10, 0.8 M NaCl, 10 mM phosphate buffer (pH 6.0)] and gently shaken at 30° C. for 3 hours. Hypha not lyzed were removed using the 3G3 glass filter, and the resulting filtrate was centrifuged at 700×g (2,000 r.p.m.) for 5 minutes to give protoplasts.

The protoplasts were washed twice with 0.8 M NaCl and once with solution I [0.8 M NaCl, 10 mM $CaCl_2$, 50 mM Tris-HCl (pH 7.5)], and then suspended in 4/5 volumes of solution I at a final concentration of $2.5 \times 10^8$ protoplasts/ml. To the suspension was added 1/5 volumes of solution II [40% (w/v) PEG 4000, 50 mM Tris-HCl (pH 7.5)], thereby preparing a protoplast suspension for use in transformation.

In the case of the protoplast suspension derived from *Aspergillus niger* SK57 or *Aspergillus nidulans* MD-4, 20 μl plasmid pANPHY1, or 10 μl each of plasmids pANPHY 1 and p3SR2, were added to 0.2 ml of the protoplast suspension, and the mixture was left on ice for 30 minutes, and 1 ml of solution II was added thereto and left at room temperature for 20 minutes. Thereafter, 10 ml of solution I was added and centrifuged at 700×g for 5 minutes to give a precipitated fraction. The precipitated fraction was suspended in 0.2 ml of solution I. The resulting suspension was applied to a CD plate medium (1% sucrose, 10 mM acetamide, 0.1% $KH_2PO_4$, 0.05% $MgSO_4.7H_2O$, 0.05% KCl) containing 0.8 M NaCl, and a medium containing 0.5% agar was layered thereon, followed by culture at 30° C. for 5 to 10 days.

In the case of the protoplast suspension derived from *Aspergillus oryzae* M-23, 10 μl of pANPHY1 and 10 μl of pSal23 were added to 0.2 ml of the protoplast suspension, and the mixture was left on ice for 30 minutes, and 1 ml of solution II was added thereto and left at room temperature for 20 minutes. Thereafter, 10 ml of solution I was added thereto, and the solution was centrifuged at 700×g for 5 minutes to give a precipitated fraction. The precipitated fraction was suspended in 0.2 ml of solution I. The suspension was applied to a minimum plate medium (1% sucrose, 0.3% $NaNO_3$, 0.1% $KH_2PO_4$, 0.05% $MgSO_4.7H_2O$, 0.05% KCl, pH 5.5), and a medium containing 0.5% agar was layered thereon, followed by culture at 30° C. for 5 to 10 days.

During cultivation, well growing strains were selected as transformants, the phytase activity of each transformant was measured, and *Aspergillus niger* MH-PA1, *Aspergillus nidulans* M-PA1 and *Aspergillus oryzae* MO-PG3 with higher activity were obtained. *Aspergillus niger* MH-PA1 and *Aspergilius nidulans* M-PA1 were deposited respectively as FERM BP-5372 and FERM BP-5373 on Jan. 25, 1996 with the National Institute of Bioscience and Human-Technology, Agency of Industrial Science and Technology, 1–3, Higashi 1-chome, Tsukuba-shi, Ibaraki-ken, 305 Japan.

Example 4
Production of Phyases by Transformants (1) Production of phytase by *Aspergillus niger* MH-PA1

Ten g of wheat bran was introduced into a 500-ml Erlenmeyer flask, and the flask was sealed with a cotton stopper and sterilized at 120° C. for 20 minutes, and 8 ml of distilled water was added thereto. The strain MH-PA1 was inoculated into the medium, and the flask was shaken so that the MH-PA1 hypha were completely mixed with the wheat bran, and subjected to stationary culture at 30° C. for 4 to 5 days.

Water 100 ml at about 37° C. was put in the flask, and the flask was left at 37° C. for 1 to 2 hours. Thereafter, the liquid was separated from solids through a No. 2 filter paper, whereby 560 U of the novel phytase was obtained. Production of the novel phytase by MH-PA1 was about 2.4-fold higher than that by the strain SK57 shown in Example 6-1.

(2) Production of phytase by *Aspergillus nidulans* M-PA1

Ten ml of phytase production medium (1% sucrose, 0.2% $NaNO_3$, 0.05% $MgSO_4.7H_2O$, 0.05% KCl, 0.001% $FeSO_4.7H_2O$, 0.1% C.S.L., pH 5.5) was put in a 100-ml Erlenmeyer flask, and the flask was sealed with a silicon stopper and sterilized at 120° C. for 20 minutes. The strain M-PA1 was inoculated into the medium and then cultured under shaking at 30° C. for 4 to 5 days.

The transformant M-PA1 produced 90 mU of phytase whose level was about 18-fold higher than 5 mU of phytase from *Aspergillus nidulans* MD-4 produced under the same conditions.

(3) Production of phytase by *Aspergillus oryzae* MO-PG3

Phytase production medium 500 ml was put in a 2-L Erlenmeyer flask which was then sealed with a cotton stopper and sterilized at 120° C. for 20 minutes. The strain MO-PG3 was inoculated into the medium and then subjected to shake culture at 28° C. for 4 to 5 days.

The transformant MO-PG3 produced 370 mU/ml phytase which was about 29-fold higher than 13 mU/ml phytase from *Aspergillus oryzae* M-23 produced under the same conditions.

Example 5
Preparation of Mutant *Aspergillus niger* SK92 Highly producing Novel Phytase from *Aspergillus niger* SK57

*Aspergillus niger* SK57 was grown on a minimum agar medium [2% sucrose, 0.3% sodium nitrate, 0.05% potassium chloride, 0.05% magnesium sulfate, 2% agar, pH 5.5] to form spores. The spores were suspended in 10 ml of sterilized water. The suspension was prepared at a final concentration of $10^7$ spores/ml in sterilized water, and 10 ml of the spore suspension was subjected to mutagenesis. The spore suspension was irradiated with UV-rays and γ-rays at 99% lethal level, thereby inducing mutation. By this mutagenesis, one strain highly producing phytase was obtained. This strain was further subjected 7 times to mutagenesis whereby *Aspergillus niger* SK92 highly producing the novel phytase was obtained.

Example 6
Production of Novel Phytase by *Aspergillus niger* SK57 and *Aspergillus niger* SK92

(1) Production of novel phytase by the strains SK57 and SK92

Ten g of wheat bran was put in a 500-ml Erlenmeyer flask, and the flask was sealed with a cotton stopper and sterilized at 120° C. for 20 minutes, and 8 ml of distilled water was added thereto. The strains SK57 or SK92 was inoculated into the medium, and the flask was shaken so that the hypha were completely mixed with the wheat bran.

Water 100 ml at about 37° C. was put in the flask which was then left at 37° C. for 1 to 2 hours. Thereafter, the liquid was separated from solids through a No. 2 filter paper.

By this production, 230 U of the novel phytase was obtained from the SKS7 and 1000 U of the novel phytase from the SK92.

Level of the novel phytase produced by SK92 was about 4.5-fold higher than that by SK57.

(2) Production of novel phytase by SK57

The strain SK57 previously grown in pure culture was inoculated into 7,500 kg of wheat bran steamed at 120° C. for 30 minutes, and the hypha and bran medium were mixed uniformly in a mixer.

The mixture was poured onto 1,500 aluminum trays (600×1,000 mm) in an amount of 5 kg/tray, and the SK57 was cultured for 5 days in a culture chamber at 30° C. under 100% humidity.

The culture was transferred to an extraction bath and sprayed with 18-ton warm water. The phytase extract was then recovered into a 25-ton tank. The extract was transferred to a vacuum-concentration tank (Nippon Shinku K. K.) where it was concentrated 2 to 3-fold under vacuum, and 3.5 tons of 95% cold ethanol was added. Impurities insolubilized by this operation were removed by a press filter.

The resulting filtrate was filtered through a germ-free filter (0.45 μm, Nippon Rosuiki K. K.), and 17.5 tons of 95% cold ethanol was added again thereto to insolubilize novel phytase. The insolubilized phytase was precipitated to give 3 tons of a precipitated fraction containing the novel phytase.

Eight tons of 95% cold ethanol was added to the precipitated fraction, and after dehydration, the insolubilized phytase was precipitated whereby 3 tons of the precipitated fraction containing the novel phytase was obtained. The dehydration and precipitation procedures were repeated 2 or 3 times, and the precipitate was dried under vacuum to give 150 million U of crude phytase powder.

Example 7
Purification of the Novel Phytase (1) Purification of the novel phytase produced by *Aspergillus niger* SK57

Ten g of the crude phytase powder obtained in Example 6-2 was dissolved in 50 ml of acetate buffer A [50 mM acetic acid/50 mM sodium acetate (pH 5.5)] and then desalted through an Ultrafilter (cut off molecular weight 10,000; Sartrius). The resulting enzyme solution was applied to a DIAION HPA-75 (Mitsubishi Corporation) column (5.6 cm×30 cm) previously equilibrated with acetate buffer A. After washed with acetate buffer A, novel phytase was eluted with acetate buffer B [50 nm acetic acid/50 mM sodium acetate (pH 4.8)] containing 0.3 M NaCl. The eluate fraction was concentrated 20-fold through an Ultrafilter (cut off molecular weight 10,000; Advantec), and then applied to an S-Sepharose FF (2.5 cm×30 cm, Pharmacia) column previously equilibrated with acetate buffer C [50 mM acetic acid/50 mM sodium acetate (pH 4.9)]. After washed with acetate buffer C, the protein was eluted with acetate buffer D [50 mM acetic acid/50 M sodium acetate (pH 5.2)] to yield a phytase fraction. The enzyme solution thus obtained was concentrated 20-fold with an Ultrafilter (cut off molecular weight 10,000; Advantec), and then applied to a Toyopearl HW-55F (Toso) column previously equilibrated with acetate buffer E [50 mM acetic acid/50 mM sodium acetate (pH 4.5)]. The novel phytase was eluted with acetate buffer E. The eluate fraction was applied to a mono-PHR 5/20 column (Pharmacia) previously equilibrated with 25 mM histidine-HCl buffer, pH 5.8 (Pharmacia), and the novel phytase was eluted with 10% Polybuffer 74-HCl, pH 4.2 (Pharmacia).

By these steps, the novel phytase was purified to a specific activity of 158 U/mg.

(2) Purification of novel phytase produced by *Aspergillus niger* MH-PA1 and *Aspergillus nidulans* M-PA1

According to the method described in Example 6-1, the strains MH-PA1 and M-PA1 were cultured, and from their respective cultures, liquid fractions (crude solutions of novel phytase) were obtained by passing through a filter paper No. 2.

Fifty mM acetate buffer A (pH 5.5) was added to each crude phytase solution which was then desalted through an Ultrafilter (cut off molecular weight 10,000, Advantec).

The desalted enzyme solution was applied to a DIAION HPA-75 column (5.6 cm×30 cm) previously equilibrated with 50 mM acetate buffer, pH 5.5. After washed with acetate buffer A, the novel phytase was eluted with acetate buffer B (pH 4.8) containing 0.3 M NaCl.

The eluate fraction was concentrated using an Ultrafilter (cut off molecular weight 10,000, Advantec) and then dialyzed. The resulting phytase fraction was applied to a Toyopearl HW-55F column (2.0 cm×60 cm) previously equilibrated with 50 mM acetate buffer E, pH 4.5, and the novel phytase was subsequently eluted with acetate buffer E.

By these steps, the novel phytase produced by *Aspergillus niger* MH-PA1 or *Aspergillus nidulans* M-PA1 was purified.

(3) Purification of novel phytase produced by *Aspergillus oryzae* MO-PG3

The microorganism was removed by centrifugation from the culture obtained in Example 4-3, and the resulting supernatant was used as the crude enzyme solution.

Fifty mM acetate buffer A (pH 5.5) was added to the crude enzyme solution which was then desalted using an Ultrafilter (cut off molecular weight 10,000, Advantec).

The desalted enzyme solution was applied to a DIAION HPA-75 column (5.6 cm×30 cm) previously equilibrated with 50 mM acetate buffer A (pH 5.5). After washed with acetate buffer A, the novel phytase was eluted with acetate buffer B (pH 4.8) containing 0.3 M NaCl.

The eluate fraction was concentrated using an Ultrafilter (cut off molecular weight 10,000, Advantec) and then dialyzed. The resulting phytase fraction was applied to a Toyopearl HW-55F column (2.0 cm×60 cm) previously equilibrated with 50 mM acetate buffer E (pH 4.5), and the novel phytase was eluted with acetate buffer E.

By these steps, the novel phytase produced by *Aspergillus oryzae* MO-PG3 was purified.

Example 8
Physicochemical Properties of Novel Phytase

The physicochemical properties of the novel phytases obtained in in Examples 7-1 to 7-3 are as follows.

(1) Km value: The activity was determined according to the standard assay where the substrate concentration was varied in the range of 0.00625 to 1.25 mM. The results were graphted out in Lineweave-Burk plot so that Km values were determined.

The Km values of the novel phytases derived from *Aspergillus niger* SK57, *Aspergillus niger* MH-PA1, *Aspergillus nidulans* M-PA1 and *Asperaillus oryzae* MO-PG3 were 13, 30, 20 and 28 $\mu$M, respectively.

The Km value of the phytase derived from *Aspergillus ficcum* NRRL3135, as determined under the same conditions, was 197 $\mu$M, so the Km values of the novel phytases of the present invention were one order of magnitude smaller than that of the known phytase.

(2) Molecular weight (by SDS-PAGE): Ten ml of sample buffer (4% 2-mercaptoethanol, 80% glycerol, 4% SDS, 40 mM Tris-HCl buffer, pH 6.8) was added to 40 ml of each novel phytase sample obtained in Examples 7-1 to 7-3, and the mixture was then boiled for 2 minutes and electrophoresed on 12.5% acrylamide gel using the AE-6200 type electrophoresis unit (Atoh). The protein was stained with Coomassie Brilliant Blue G250. Further, each sample whose carbohydrate chains have been removed by treatment with endoglycosidase H was also electrophoresed in the same manner.

Figure 3:
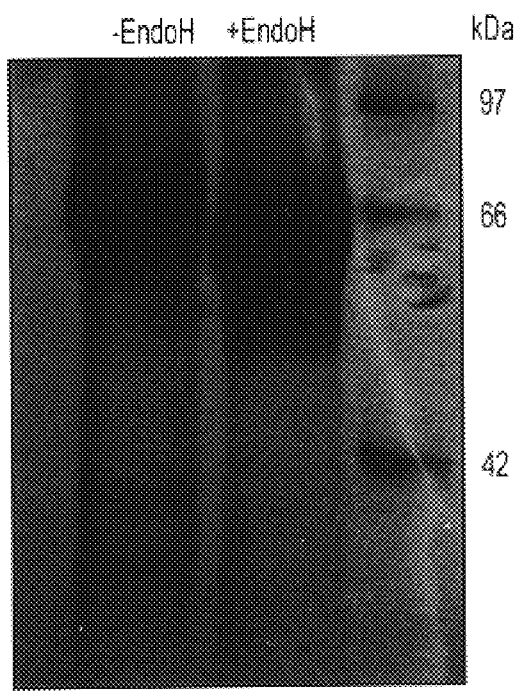
FIG. 3 shows a profile of novel phytases in SDS-PAGE for molecular-weight measurement.

A photograph showing the results of SDS-PAGE of the novel phytase from *Aspergillus niger* SK57 is shown in FIG. 3. The molecular weight of the novel phytase from the SK57 or MH-PA1 was about 60 kDa as determined by SDS-PAGE. The molecular weight of these novel phytase was hardly changed even after removal of carbohydrate chains by treatment with endoglycosidase H. The molecular weight deduced from the amino acid sequence shown in SEQ ID NO: 1 or 2 was about 50 kDa which was almost consistent with that determined by SDS-PAGE.

Figure 4:
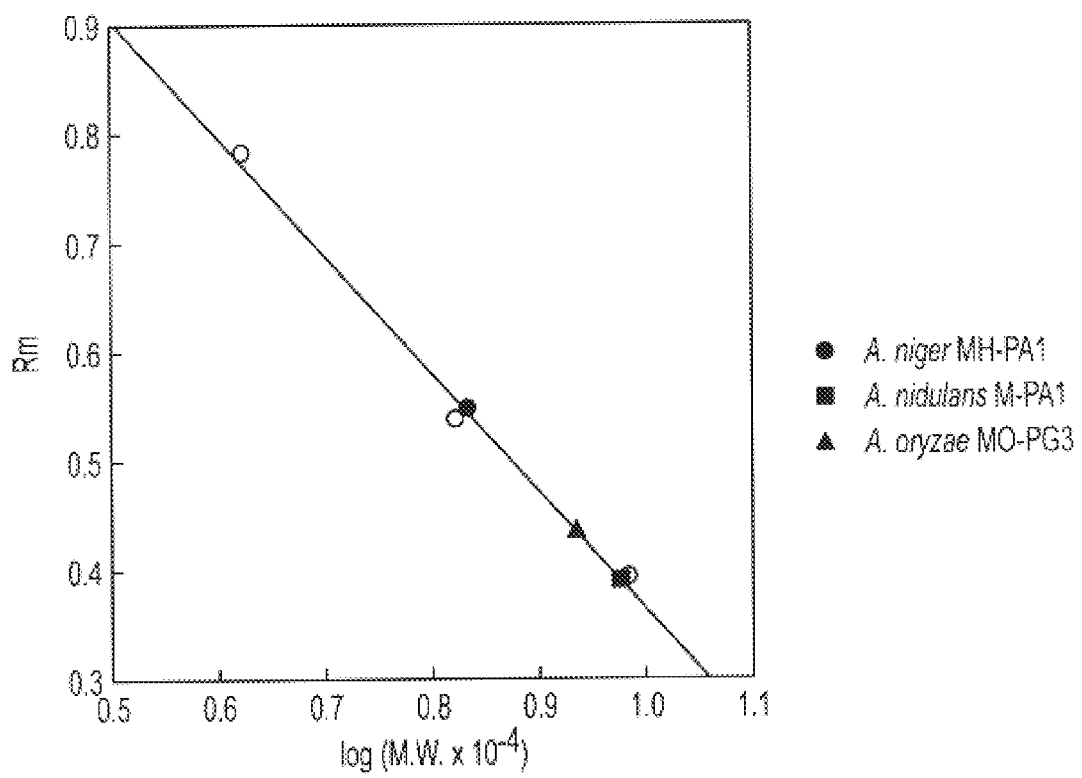
FIG. 4 shows a calibration curve obtained by measuring the molecular weight of novel phytase.

The molecular weight of novel phytases from *Aspergillus nidulans* M-PA1 and *Aspergillus oryzae* MO-PG3, as determined by SDS-PAGE, are shown in FIG. 4. In this measurement, the molecular weight of novel phytases from the 2 strains was about 90 to 100 kDa. Because these novel phytases after treated with endoglycosidase H had the same molecular weight (about 60 kDa) as that of the novel phytase from the strain SK57 or MH-PA1, it was found that the novel phytases from the M-PA1 and MO-PG3 contained carbohydrate chains.

Figure 5:
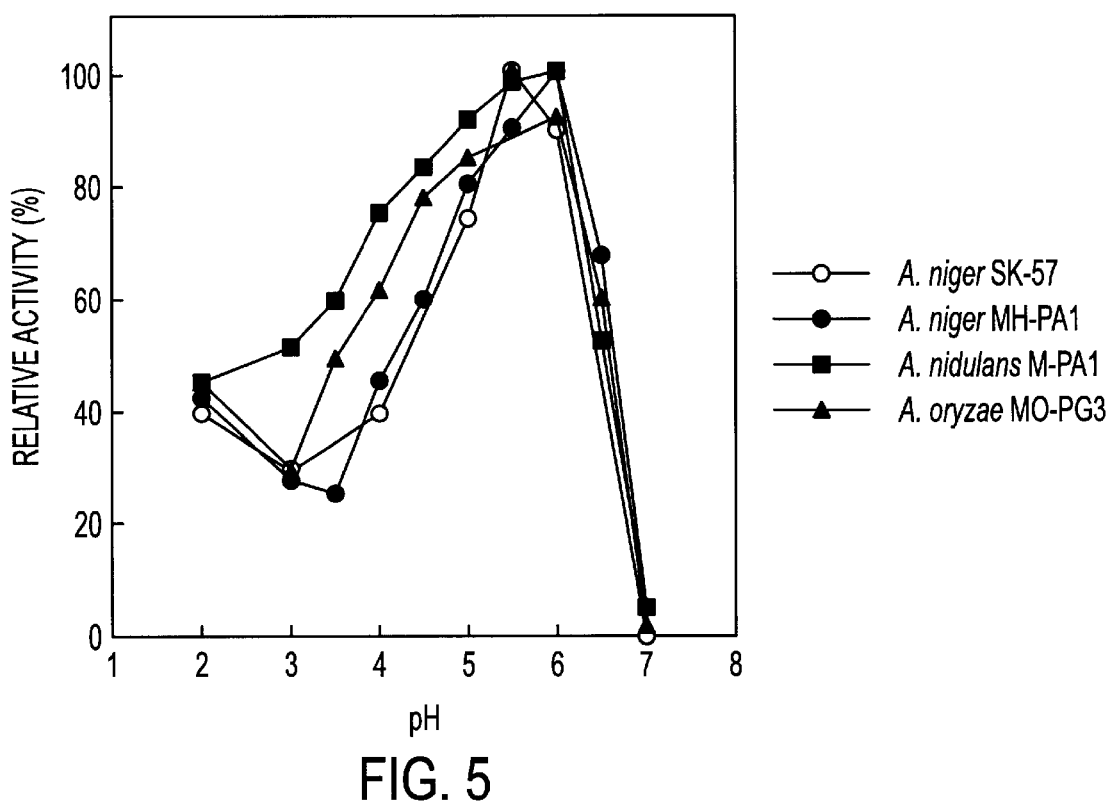
FIG. 5 shows optimum pH values for novel phytases. The activity at each pH value is exhibited as a relative activity (%) to the activity as 100% which has been determined under pH conditions conferring a maximum activity.

(3) Optimum pH: The activity was measured by the standard assay wherein the pH was varied using 0.2 M buffers shown below:
pH 2 to 4: glycine/HCl buffer
pH 4 to 5.5: acetic acid/sodium acetate buffer
pH 5.5 to 7: MES buffer (Good Buffer)
pH 7 to 8: MOPS buffer (Good Buffer)
pH 8 to 9: Tris-HCl buffer Results are shown in FIG. 5. The novel phytase of the present invention exhibited the maximum activity at pH 5.0 to 6.5. The enzyme had no activity at a pH of 7.0 or greater.

Figure 6:
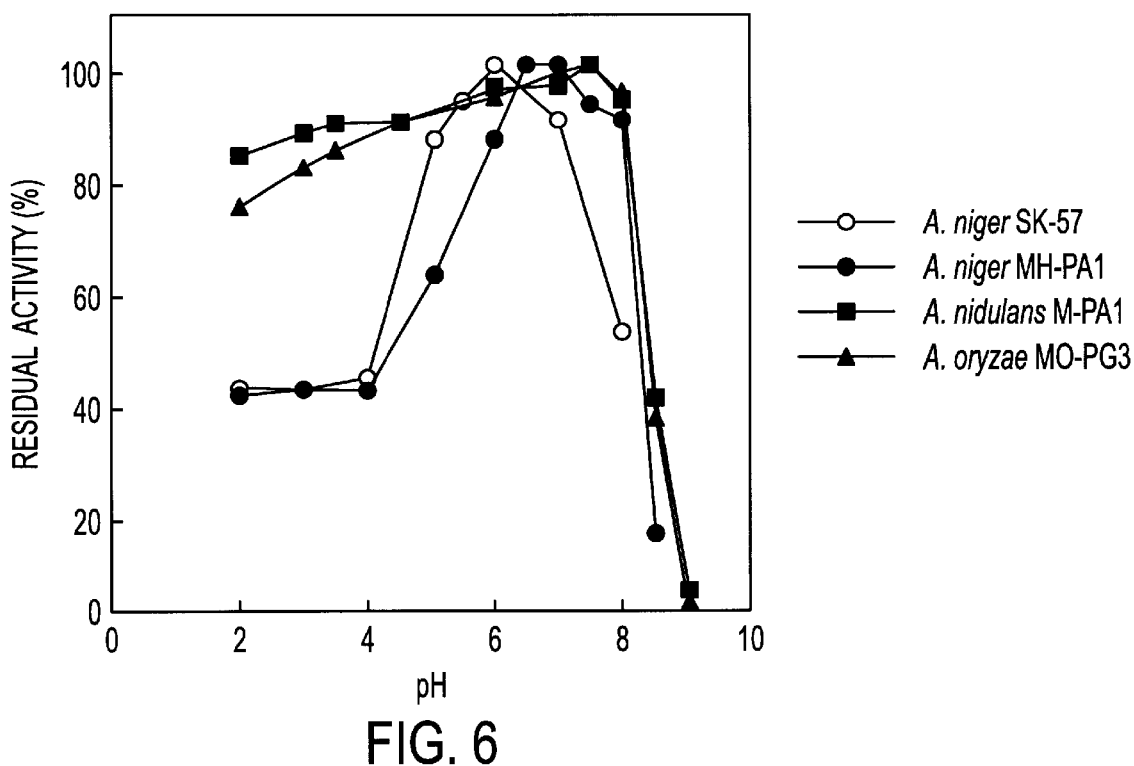
FIG. 6 shows pH stability for novel phytases.

(4) pH stability: 2.1 mg/ml novel phytase solution was kept at 37° C. for 60 minutes in 100 mM buffer shown below, and its activity was measured by the standard assay.
pH 2 to 4: glycine/HCl buffer
pH 4 to 5.5: acetic acid/sodium acetate buffer
pH 5.5 to 7: MES buffer (Good Buffer)
pH 7 to 8: MOPS buffer (Good Buffer)
pH 8 to 9: Tris-HCl buffer Results are shown in FIG. 6.

The novel phytases from *Aspergillus niger* strains SK57 and MH-PA1 had a residual activity of about 60% or more at pH 4.5 to pH 7.5.

The novel phytases from *Aspergillus nidulans* M-PAL and *Aspergillus oryzae* MO-PG3 had about 70% or more at a pH of 8 or lower.

(5) Optimum temperature: The activity was determined at a reaction temperature of 0 to 70° C. by the standard assay.

Figure 7:
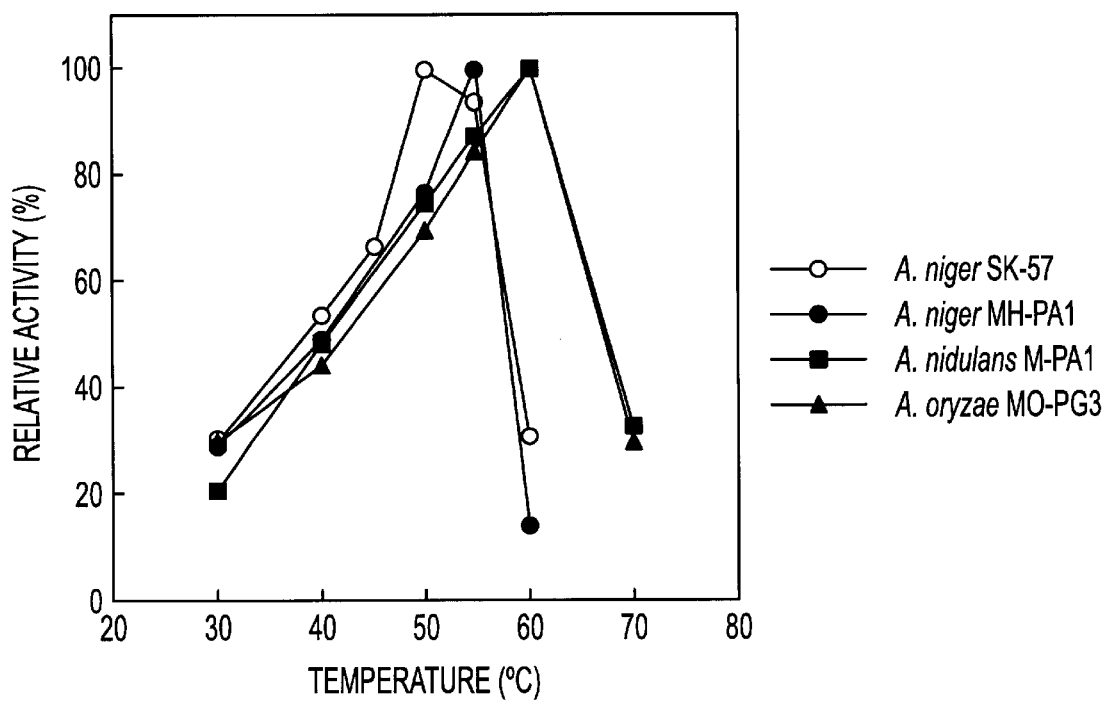
FIG. 7 shows optimum temperatures for novel phytases. The activity at each temperature is exhibited as a relative activity (%) to the activity as 100% which has been determined under conditions of temperature conferring a maximum activity.

Results are shown in FIG. 7. The novel phytases of the present invention exhibited the maximum activity at 40 to 65° C.

(6) Temperature stability: A solution of the enzyme was maintained at the protein concentration of 2.1 mg/ml at 0 to 60° C. for 60 minutes in 100 mM acetic acid/sodium acetate buffer (pH 5.5), and its activity was determined by the standard assay.

Figure 8:
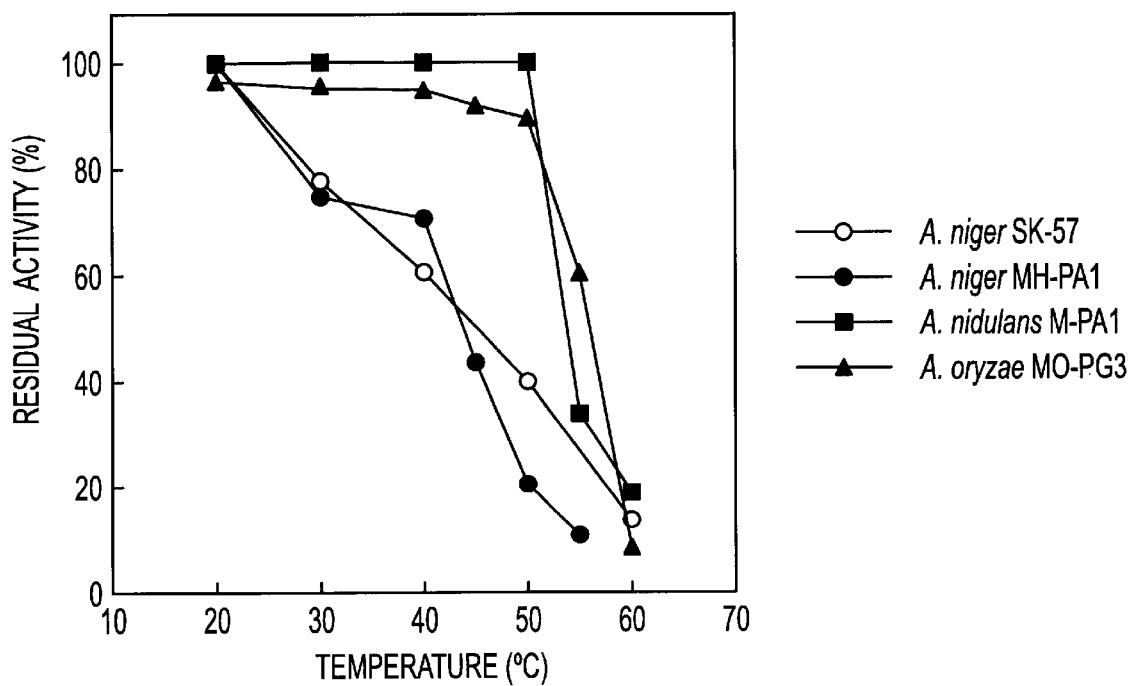
FIG. 8 shows heat stability for novel phytases. The activity at each temperature is exhibited as a relative activity (%) to the activity as 100% at 4° C.

Results are shown in FIG. 8.

The novel phytases from *Aspergillus niger* SK57 and *Aspergillus niger* MH-PA1 exhibited a relative activity of about 70% or more at a temperature of 30° C. or lower.

The novel phytases from *Aspergillus nidulans* M-PA1 and *Aspergillus oryzae* MO-PG3 were stable up to 50° C., but they were gradually inactivated at a temperature exceeding 50° C. Because the novel phytases from *Aspergilltis nidulans* M-PA1 and *Aspergillus oryzae* MO-PG3 had carbohydrate chains as shown in Example 8-1, they are thought to have higher heat stability than the novel phytases from *Aspergillus niger* SK57 and *Aspergillus niger* MH-PA1.

(7) Substrate specificity: The activity was determined by the standard assay method wherein the concentration of substrates was adjusted at 1 mM and 10 mM.

The results of the novel phytase from *Aspergillus niger* SK57 are shown in Table 1. The novel phytase acted with low specificity on the substrates shown in Table 1, but it had less activity on substrates other than phytic acid. The same results were obtained with respect to the novel phytases from other strains.

TABLE 1

| Substrate | Concentration (mM) | Relative activity (100%) |
| --- | --- | --- |
| phytic acid | 1 | 100 |
| p-nitrophenyl phosphate | 1 | 1.9 |
|  | 10 | 10 |
| D-glucose-6-phosphate | 1 | 0.45 |
|  | 10 | 4.2 |
| fructose-6-phosphate | 1 | 0.15 |
|  | 10 | 0.93 |
| D-myo-inositol 1,4,5-tris-phosphate | 1 | 0.71 |
|  | 10 | 5.8 |
| glycerophosphoric acid | 1 | 0.11 |
|  | 10 | 0.96 |
| ATP | 1 | 1.6 |
|  | 10 | 1.2 |

(8) Isoelectric focusing: Isoelectric focusing was performed on 3% acrylamide gel (Ampholine pH 3.5–10.0, Pharmacia) using the AE-3230 model electrophoresis unit (Atoh).

Figure 9:
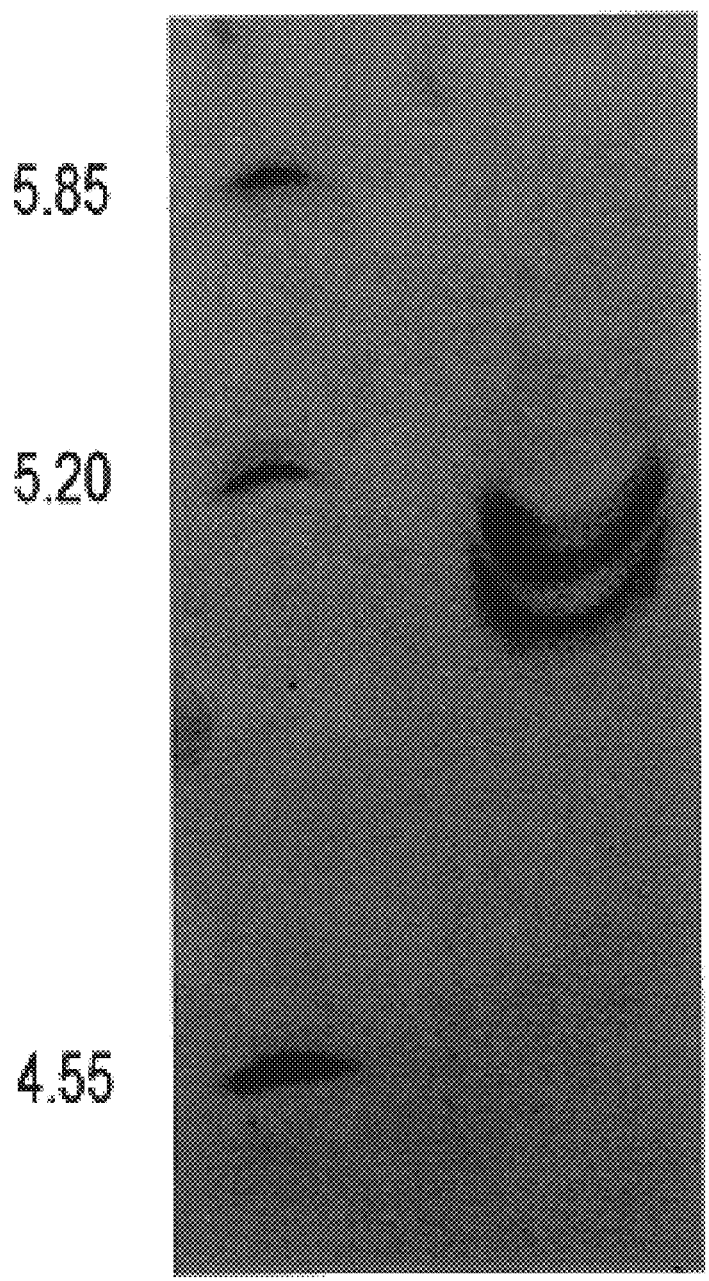
FIG. 9 shows the isoelectric point of novel phytase in isoelectric focusing.

The result of the novel phytase from *Aspergillus niger* SK57 is shown in FIG. 9. The isoelectric point (pI) of the phytase is in the range of 4.7 to 5.4.

INDUSTRIAL APPLICATION

According to the present invention, there can be provided an inexpensive phytase with a low Km value for phytic acid, DNA coding for the phytase, recombinant DNA having the DNA introduced thereinto, a microorganism carrying the recombinant DNA, and a process for preparing the phytase by use of the microorganism. This phytase can be used in feed in order to degrade phytic acid as an anti-trophic factor contained in the feed, thereby improving the nutritive value of the feed and achieving an efficient utilization of phosphoric acid released by the degradation.

What is claimed is:

1. An isolated or purified gene coding for a phytase, from a microorganism belonging to the genus Aspergillus, having the following properties:
   (1) a Michaelis constant of 10 to 30 $\mu$M when phytic acid used as the substrate;
   (2) molecular weight as determined by SDS-PAGE: about 60 kDa after treatment with endoglycosidase H;
   (3) optimum pH: 5.0 to 6.5;
   (4) optimum temperature: 45° C. to 65° C;
   (5) acting on the substrates: phytic acid, p-nitrophenylphosphate, D-glucose 6-phosphate, fructose 6-phosphate, D-myo-inositol 1,4,5-tris-phosphate, glycerol phosphate, adenosine triphosphate; and
   (6) isoelectric focusing: pI 4.7 to 5.4.

2. An isolated or purified gene according to claim 1, wherein the gene codes for a protein selected from proteins having the amino acid sequences shown in SEQ ID Nos: 1, 2, or 3, or a protein which has an amino acid sequence shown in SEQ ID Nos: 1, 2 or 3 in which one or more amino acids have been substituted, deleted or added, and said protein is encoded by a DNA that hybridizes with SEQ ID Nos 4 or 5 under stringent conditions comprising a wash step of 0.1 to 2×SSC at 65° C.

3. An isolated or purified gene according to claim 1, wherein the gene is a gene selected from the DNAs shown in SEQ ID Nos: 4 or 5.

4. An isolated or purified gene according to claim 1, wherein the microorganism belonging to the genus Aspergillus is selected from Aspergillus niger SK57 (FERM BP-5473) or Aspergillus niger SK92 (FERM BP-5481).

5. Recombinant DNA obtained by introducing into a vector a DNA fragment containing a gene coding for a phytase, from a microorganism belonging to the genus Aspergillus, having the following properties:
   (1) a Michaelis constant of 10 to 30 $\mu$M when phytic acid used as the substrate;
   (2) molecular weight as determined by SDS-PAGE: about 60 kDa after treatment with endoglycosidase H;
   (3) optimum pH: 5.0 to 6.5;
   (4) optimum temperature: 45° C. to 65° C;
   (5) acting on the substrates: phytic acid, p-nitrophenylphosphate, D-glucose 6-phosphate, fructose 6-phosphate, D-myo-inositol 1,4,5-tris-phosphate, glycerol phosphate, adenosine triphosphate; and
   (6) isoelectric focusing: pI 4.7 to 5.4.

6. Recombinant DNA according to claim 5, wherein the gene codes for a protein selected from proteins having the amino acid sequences shown in SEQ ID Nos: 1, 2 or 3, or a protein which has an amino acid sequence shown in SEQ ID Nos: 1, 2 or 3 in which one or more amino acids have been substituted, deleted or added, and said protein is encoded by a DNA that hybridizes with SEQ ID Nos 4 or 5 under stringent conditions comprising a wash step of 0.1 to 2×SSC at 65° C.

7. Recombinant DNA according to claim 5, wherein the gene is selected from the DNAs shown in SEQ ID Nos: 4 or 5.

8. Recombinant DNA according to claim 5, wherein the microorganism belonging to the genus Aspergillus is selected from Aspergillus niger SK57 (FERM BP-5473) or Aspergillus niger SK92 (FERM BP-5481).

9. Recombinant DNA according to claim 5, wherein the recombinant DNA is pANPHY1.

10. A transformant carrying recombinant DNA obtained by introducing into a vector a DNA fragment containing a gene coding for a phytase, from a microorganism belonging to the genus Aspergillus, having the following properties:
    (1) a Michaelis constant of 10 to 30 $\mu$M when phytic acid used as the substrate;

(2) molecular weight as determined by SDS-PAGE: about 60 kDa after treatment with endoglycosidase H;

(3) optimum pH: 5.0 to 6.5;

(4) optimum temperature: 45° C. to 65° C;

(5) acting on the substrates: phytic acid, p-nitrophenylphosphate, D-glucose 6-phosphate, fructose 6-phosphate, D-myo-inositol 1,4,5-tris-phosphate, glycerol phosphate, adenosine triphosphate; and (6) isoelectric focusing: pI 4.7 to 5.4.

11. A transformant according to claim 10, wherein the gene codes for a protein selected from proteins having the amino acid sequences shown in SEQ ID Nos: 1, 2 or 3, or a protein which has an amino acid sequence shown iin SEQ ID Nos: 1, 2 or 3 in which one or more amino acids have been substituted, deleted or added, and said protein is encoded by a DNA that hybridizes with SEQ ID Nos: 4 or 5 under stringent conditions comprising a wash step of 0.1 to 2×SSC at 65° C.

12. A transformant according to claim 10, wherein the gene is selected from the DNAs shown in SEQ ID Nos: 4 or 5.

13. A transformant according to claim 10, wherein the microorganism belonging to the genus Aspergillus is selected from *Aspergillus niger* SK57 (FERM BP-5473) or *Aspergillus niger* SK92 (FERM BP-5481).

14. A transformant according to claim 10, wherein the recombinant DNA is pANPHY1.

15. A transformant according to claim 10, wherein the transformant is selected from the group consisting of microorganisms belonging to the genera Escherichia, Serratia, Corynebacterium, Brevibacterium, Pseudomonas, Bacillus, Aspergillus, Rhizopus, Tricchoderma, Neurospora, Mucor, Penicillium, Kluyveromyces, Saccharomyces and Schizosaccharomyces.

16. A transformant according to claim 10, wherein the transformant is selected from the group consisting of *Aspergillus niger* MH-PA1 (FERM BP-5372), *Aspergillus nidulans* M-PA1 (FERM BP-5373).

17. A process for preparing a phytase from a microorganism belonging to the genus Aspergillus, wherein the microorganism is a transformant carrying recombinant DNA obtained by introducing into a vector a DNA fragment containing a gene coding for a phytase, from said microorganism, having the following properties:

(1) a Michaelis constant of 10 to 30 $\mu$M when phytic acid used as the substrate;

(2) molecular weight as determined by SDS-PAGE: about 60 kDa after treatment with endoglycosidase H;

(3) optimum pH: 5.0 to 6.5;

(4) optimum temperature: 45° C. to 65° C;

(5) acting on the substrates: phytic acid, p-nitrophenylphosphate, D-glucose 6-phosphate, fructose 6-phosphate, D-myo-inositol 1,4,5-tris-phosphate, glycerol phosphate, adenosine triphosphate; and (6) isoelectric focusing: pI 4.7 to 5.4, wherein said process comprises culturing in a medium said microorganism, producing and accumulating phytase in said medium, and then recovering phytase from said medium.

18. A process according to claim 17, wherein the gene codes for a protein selected from proteins having the amino acid sequences shown in SEQ ID Nos: 1, 2 or 3, or a protein which has an amino acid sequence shown in SEQ ID Nos: 1, 2 or 3 in which one or more amino acids have been substituted, deleted or added and said protein is encoded by a DNA that hybridizes with SEQ ID Nos: 4 or 5 under stringent conditions comprising a wash step of 0.1 to 2×SSC at 65° C.

19. A process according to claim 17, wherein the gene is selected from the DNAs shown in SEQ ID Nos: 4 or 5.

20. A process according to claim 17, wherein the microorganism belonging to the genus Aspergillus is selected from *Aspergillus niger* SK57 (FERM BP-5473) or *Aspergillus niger* SK92 (FERM BP-5481).

21. A process according to claim 17, wherein the recombinant DNA is pANPHY1.

22. A process according to claim 17, wherein the transformant is selected from the group consisting of microorganisms belonging to the genera Escherichia, Serratia, Corynebacterium, Brevibacterium, Pseudomonas, Bacillus, Aspergillus, Rhizopus, Tricchoderma, Neurospora, Mucor, Penicillium, Kluyveromyces, Saccharomyces and Schizosaccharomyces.

23. A process according to claim 17, wherein the transformant is selected from the group consisting of *Aspergillus niger* MH-PA1 (FERM BP-5372), *Aspergillus nidulans* M-PA1 (FERM BP-5373).

* * * * *

SEQUENCE LISTING

<160> NUMBER OF SEQ ID NOS: 7

<210> SEQ ID NO 1
<211> LENGTH: 443
<212> TYPE: PRT
<213> ORGANISM: Aspergillus niger

<400> SEQUENCE: 1

```
Ser Arg Asn Gln Ser Thr Cys Asp Thr Val Asp Gln Gly Tyr Gln Cys
 1               5                  10                  15

Phe Ser Glu Thr Ser His Leu Trp Gly Gln Tyr Ala Pro Phe Phe Ser
            20                  25                  30

Leu Ala Asn Lys Ser Ala Ile Ser Pro Asp Val Pro Ala Gly Cys His
        35                  40                  45

Val Thr Phe Ala Gln Val Leu Ser Arg His Gly Ala Arg Tyr Pro Thr
    50                  55                  60

Asp Ser Lys Gly Lys Lys Tyr Ser Ala Leu Ile Glu Glu Ile Gln Gln
 65                  70                  75                  80

Asn Ala Thr Thr Phe Glu Gly Lys Tyr Ala Phe Leu Lys Thr Tyr Asn
                85                  90                  95

Tyr Ser Leu Gly Ala Asp Asp Leu Thr Pro Phe Gly Glu Gln Glu Leu
            100                 105                 110

Val Asn Ser Gly Val Lys Phe Tyr Gln Arg Tyr Glu Ser Leu Thr Arg
        115                 120                 125

Asn Ile Val Pro Phe Ile Arg Ser Ser Gly Ser Ser Arg Val Ile Ala
130                 135                 140

Ser Gly Asn Lys Phe Ile Glu Gly Phe Gln Ser Thr Lys Leu Lys Asp
145                 150                 155                 160

Pro Arg Ala Gln Pro Gly Gln Ser Ser Pro Lys Ile Asp Val Val Ile
                165                 170                 175

Ser Glu Ala Ser Thr Ser Asn Asn Thr Leu Asp Pro Gly Thr Cys Thr
            180                 185                 190

Val Phe Glu Asp Ser Glu Leu Ala Asp Asp Ile Glu Ala Asn Phe Thr
        195                 200                 205

Ala Thr Phe Val Pro Ser Ile Arg Gln Arg Leu Glu Asn Asp Leu Ser
    210                 215                 220

Gly Val Ser Leu Thr Asp Thr Glu Val Thr Tyr Leu Met Asp Met Cys
225                 230                 235                 240

Ser Phe Asp Thr Ile Ser Thr Ser Thr Val Asp Thr Lys Leu Ser Pro
                245                 250                 255

Phe Cys Asp Leu Phe Thr His Glu Glu Trp Ile Asn Tyr Asp Tyr Leu
            260                 265                 270

Gln Ser Leu Asn Lys Tyr Tyr Gly His Gly Ala Gly Asn Pro Leu Gly
        275                 280                 285

Pro Thr Gln Gly Val Gly Tyr Ala Asn Glu Leu Ile Ala Arg Leu Thr
    290                 295                 300

His Ser Pro Val His Asp Asp Thr Ser Ser Asn His Thr Leu Asp Ser
305                 310                 315                 320
```

```
Asn Pro Ala Thr Phe Pro Leu Asn Ser Thr Leu Tyr Ala Asp Phe Ser
                325                 330                 335

His Asp Asn Gly Ile Ile Ser Ile Leu Phe Ala Leu Gly Leu Tyr Asn
            340                 345                 350

Gly Thr Lys Pro Leu Ser Ser Thr Ala Glu Asn Ile Thr Gln Thr
        355                 360                 365

Asp Gly Phe Ser Ser Ala Trp Thr Val Pro Phe Ala Ser Arg Met Tyr
    370                 375                 380

Val Glu Met Met Gln Cys Gln Ser Glu Gln Pro Leu Val Arg Val
385             390                 395                 400

Leu Val Asn Asp Arg Val Val Pro Leu His Gly Cys Pro Val Asp Ala
                405                 410                 415

Leu Gly Arg Cys Thr Arg Asp Ser Phe Val Lys Gly Leu Ser Phe Ala
                420                 425                 430

Arg Ser Gly Gly Asp Trp Gly Glu Cys Phe Ala
            435                 440

<210> SEQ ID NO 2
<211> LENGTH: 443
<212> TYPE: PRT
<213> ORGANISM: Aspergillus niger
<220> FEATURE:
<223> OTHER INFORMATION: Xaa at positions 2 & 3 may be any amino acid or
      unknown

<400> SEQUENCE: 2

Ser Xaa Xaa Gln Ser Thr Cys Asp Thr Val Asp Gln Gly Tyr Gln Cys
 1               5                  10                  15

Phe Ser Glu Thr Ser His Leu Trp Gly Gln Tyr Ala Pro Phe Phe Ser
            20                  25                  30

Leu Ala Asn Lys Ser Ala Ile Ser Pro Asp Val Pro Ala Gly Cys His
        35                  40                  45

Val Thr Phe Ala Gln Val Leu Ser Arg His Gly Ala Arg Tyr Pro Thr
    50                  55                  60

Asp Ser Lys Gly Lys Lys Tyr Ser Ala Leu Ile Glu Glu Ile Gln Gln
65                  70                  75                  80

Asn Ala Thr Thr Phe Glu Gly Lys Tyr Ala Phe Leu Lys Thr Tyr Asn
                85                  90                  95

Tyr Ser Leu Gly Ala Asp Asp Leu Thr Pro Phe Gly Glu Gln Glu Leu
            100                 105                 110

Val Asn Ser Gly Val Lys Phe Tyr Gln Arg Tyr Glu Ser Leu Thr Arg
        115                 120                 125

Asn Ile Val Pro Phe Ile Arg Ser Ser Gly Ser Ser Arg Val Ile Ala
    130                 135                 140

Ser Gly Asn Lys Phe Ile Glu Gly Phe Gln Ser Thr Lys Leu Lys Asp
145                 150                 155                 160

Pro Arg Ala Gln Pro Gly Gln Ser Ser Pro Lys Ile Asp Val Val Ile
                165                 170                 175

Ser Glu Ala Ser Thr Ser Asn Asn Thr Leu Asp Pro Gly Thr Cys Thr
            180                 185                 190

Val Phe Glu Asp Ser Glu Leu Ala Asp Asp Ile Glu Ala Asn Phe Thr
        195                 200                 205

Ala Thr Phe Val Pro Ser Ile Arg Gln Arg Leu Glu Asn Asp Leu Ser
    210                 215                 220

Gly Val Ser Leu Thr Asp Thr Glu Val Thr Tyr Leu Met Asp Met Cys
```

```
                 225                 230                 235                 240
Ser Phe Asp Thr Ile Ser Thr Ser Thr Val Asp Thr Lys Leu Ser Pro
                245                 250                 255

Phe Cys Asp Leu Phe Thr His Glu Glu Trp Ile Asn Tyr Asp Tyr Leu
            260                 265                 270

Gln Ser Leu Asn Lys Tyr Tyr Gly His Gly Ala Gly Asn Pro Leu Gly
        275                 280                 285

Pro Thr Gln Gly Val Gly Tyr Ala Asn Glu Leu Ile Ala Arg Leu Thr
    290                 295                 300

His Ser Pro Val His Asp Asp Thr Ser Ser Asn His Thr Leu Asp Ser
305                 310                 315                 320

Asn Pro Ala Thr Phe Pro Leu Asn Ser Thr Leu Tyr Ala Asp Phe Ser
                325                 330                 335

His Asp Asn Gly Ile Ile Ser Ile Leu Phe Ala Leu Gly Leu Tyr Asn
            340                 345                 350

Gly Thr Lys Pro Leu Ser Ser Thr Thr Ala Glu Asn Ile Thr Gln Thr
        355                 360                 365

Asp Gly Phe Ser Ser Ala Trp Thr Val Pro Phe Ala Ser Arg Met Tyr
    370                 375                 380

Val Glu Met Met Gln Cys Gln Ser Glu Gln Glu Pro Leu Val Arg Val
385                 390                 395                 400

Leu Val Asn Asp Arg Val Val Pro Leu His Gly Cys Pro Val Asp Ala
                405                 410                 415

Leu Gly Arg Cys Thr Arg Asp Ser Phe Val Lys Gly Leu Ser Phe Ala
            420                 425                 430

Arg Ser Gly Gly Asp Trp Gly Glu Cys Phe Ala
        435                 440

<210> SEQ ID NO 3
<211> LENGTH: 467
<212> TYPE: PRT
<213> ORGANISM: Aspergillus niger

<400> SEQUENCE: 3

Met Gly Val Ser Ala Val Leu Leu Pro Leu Tyr Leu Leu Ser Gly Val
  1               5                  10                  15

Thr Ser Gly Leu Ala Val Pro Ala Ser Arg Asn Gln Ser Thr Cys Asp
             20                  25                  30

Thr Val Asp Gln Gly Tyr Gln Cys Phe Ser Glu Thr Ser His Leu Trp
         35                  40                  45

Gly Gln Tyr Ala Pro Phe Phe Ser Leu Ala Asn Lys Ser Ala Ile Ser
     50                  55                  60

Pro Asp Val Pro Ala Gly Cys His Val Thr Phe Ala Gln Val Leu Ser
 65                  70                  75                  80

Arg His Gly Ala Arg Tyr Pro Thr Asp Ser Lys Gly Lys Lys Tyr Ser
                 85                  90                  95

Ala Leu Ile Glu Glu Ile Gln Gln Asn Ala Thr Thr Phe Glu Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Val Lys Phe Tyr
    130                 135                 140

Gln Arg Tyr Glu Ser Leu Thr Arg Asn Ile Val Pro Phe Ile Arg Ser
145                 150                 155                 160
```

-continued

```
Ser Gly Ser Ser Arg Val Ile Ala Ser Gly Asn Lys Phe Ile Glu Gly
            165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Thr Ser Asn Asn
            195                 200                 205

Thr Leu Asp Pro Gly Thr Cys Thr Val Phe Glu Asp Ser Glu Leu Ala
            210                 215                 220

Asp Asp Ile Glu Ala Asn Phe Thr Ala Thr Phe Val Pro Ser Ile Arg
225                 230                 235                 240

Gln Arg Leu Glu Asn Asp Leu Ser Gly Val Ser Leu Thr Asp Thr Glu
            245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Glu
            275                 280                 285

Glu Trp Ile Asn Tyr Asp Tyr Leu Gln Ser Leu Asn Lys Tyr Tyr Gly
            290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
            325                 330                 335

Ser Ser Asn His Thr Leu Asp Ser Asn Pro Ala Thr Phe Pro Leu Asn
            340                 345                 350

Ser Thr Leu Tyr Ala Asp Phe Ser His Asp Asn Gly Ile Ile Ser Ile
            355                 360                 365

Leu Phe Ala Leu Gly Leu Tyr Asn Gly Thr Lys Pro Leu Ser Ser Thr
            370                 375                 380

Thr Ala Glu Asn Ile Thr Gln Thr Asp Gly Phe Ser Ser Ala Trp Thr
385                 390                 395                 400

Val Pro Phe Ala Ser Arg Met Tyr Val Glu Met Met Gln Cys Gln Ser
            405                 410                 415

Glu Gln Glu Pro Leu Val Arg Val Leu Val Asn Asp Arg Val Val Pro
            420                 425                 430

Leu His Gly Cys Pro Val Asp Ala Leu Gly Arg Cys Thr Arg Asp Ser
            435                 440                 445

Phe Val Lys Gly Leu Ser Phe Ala Arg Ser Gly Gly Asp Trp Gly Glu
            450                 455                 460

Cys Phe Ala
465

<210> SEQ ID NO 4
<211> LENGTH: 1332
<212> TYPE: DNA
<213> ORGANISM: Aspergillus niger
<220> FEATURE:
<221> NAME/KEY: CDS
<222> LOCATION: (1)..(1332)

<400> SEQUENCE: 4 tcg aga aat caa tcc act tgc gat acg gtc gat cag ggg tat caa tgc     48
Ser Arg Asn Gln Ser Thr Cys Asp Thr Val Asp Gln Gly Tyr Gln Cys
  1               5                  10                  15 ttc tcg gag act tcg cat ctt tgg ggc caa tac gcg ccg ttc ttt tct     96
Phe Ser Glu Thr Ser His Leu Trp Gly Gln Tyr Ala Pro Phe Phe Ser
             20                  25                  30
```

-continued

```
ctg gca aac aaa tcg gcc atc tcc cct gat gtt cct gcc gga tgc cat      144
Leu Ala Asn Lys Ser Ala Ile Ser Pro Asp Val Pro Ala Gly Cys His
         35                  40                  45 gtc act ttc gcc cag gtt ctc tcc cgc cat gga gca cgg tat ccg acc      192
Val Thr Phe Ala Gln Val Leu Ser Arg His Gly Ala Arg Tyr Pro Thr
 50                  55                  60 gac tcc aag ggc aag aaa tac tcc gct ctc atc gag gag atc cag cag      240
Asp Ser Lys Gly Lys Lys Tyr Ser Ala Leu Ile Glu Glu Ile Gln Gln
 65                  70                  75                  80 aac gcg aca acc ttc gag ggg aaa tat gcc ttc ctg aag aca tac aac      288
Asn Ala Thr Thr Phe Glu Gly Lys Tyr Ala Phe Leu Lys Thr Tyr Asn
                 85                  90                  95 tac agc ctg ggc gcg gat gat ctg act ccc ttc gga gag cag gag ctg      336
Tyr Ser Leu Gly Ala Asp Asp Leu Thr Pro Phe Gly Glu Gln Glu Leu
            100                 105                 110 gtc aac tcc ggc gtc aag ttc tac cag cga tac gaa tcg ctc aca aga      384
Val Asn Ser Gly Val Lys Phe Tyr Gln Arg Tyr Glu Ser Leu Thr Arg
            115                 120                 125 aac att gtc ccg ttc atc cga tcc tca ggc tcc agc cgc gtg att gcc      432
Asn Ile Val Pro Phe Ile Arg Ser Ser Gly Ser Ser Arg Val Ile Ala
130                 135                 140 tct ggc aat aaa ttc atc gag ggc ttc cag agc act aag ctg aag gat      480
Ser Gly Asn Lys Phe Ile Glu Gly Phe Gln Ser Thr Lys Leu Lys Asp
145                 150                 155                 160 cct cgt gcc cag ccc ggc caa tcg tcg ccc aag atc gac gtg gtc att      528
Pro Arg Ala Gln Pro Gly Gln Ser Ser Pro Lys Ile Asp Val Val Ile
                165                 170                 175 tca gag gcc agc aca tcc aac aac act ctc gat ccg ggc acc tgc acc      576
Ser Glu Ala Ser Thr Ser Asn Asn Thr Leu Asp Pro Gly Thr Cys Thr
                180                 185                 190 gtt ttc gaa gat agc gaa ttg gcc gat gac atc gaa gcc aat ttc acc      624
Val Phe Glu Asp Ser Glu Leu Ala Asp Asp Ile Glu Ala Asn Phe Thr
            195                 200                 205 gcc acg ttc gtc ccc tcc att cgt caa cgt ctg gag aac gac ttg tct      672
Ala Thr Phe Val Pro Ser Ile Arg Gln Arg Leu Glu Asn Asp Leu Ser
210                 215                 220 ggc gtg tct ctc acg gac aca gaa gtg acc tac ctc atg gac atg tgc      720
Gly Val Ser Leu Thr Asp Thr Glu Val Thr Tyr Leu Met Asp Met Cys
225                 230                 235                 240 tcc ttc gac acc atc tcc acc agc acc gtc gac acc aag ctg tcc ccc      768
Ser Phe Asp Thr Ile Ser Thr Ser Thr Val Asp Thr Lys Leu Ser Pro
                245                 250                 255 ttc tgt gac ctg ttc acc cat gaa gaa tgg atc aac tac gac tac ctc      816
Phe Cys Asp Leu Phe Thr His Glu Glu Trp Ile Asn Tyr Asp Tyr Leu
                260                 265                 270 cag tcc ctg aac aaa tac tac ggc cat ggc gca ggt aac ccg ctc ggc      864
Gln Ser Leu Asn Lys Tyr Tyr Gly His Gly Ala Gly Asn Pro Leu Gly
            275                 280                 285 ccg acc cag ggc gtc ggc tac gct aac gag ctc atc gcc cgt ctc acc      912
Pro Thr Gln Gly Val Gly Tyr Ala Asn Glu Leu Ile Ala Arg Leu Thr
        290                 295                 300 cac tcg cct gtc cac gat gac acc agc tcc aac cac aca ttg gac tcc      960
His Ser Pro Val His Asp Asp Thr Ser Ser Asn His Thr Leu Asp Ser
305                 310                 315                 320 aac ccg gct act ttc ccg ctc aac tcc act ctc tat gcg gac ttt tcg      1008
Asn Pro Ala Thr Phe Pro Leu Asn Ser Thr Leu Tyr Ala Asp Phe Ser
                325                 330                 335 cat gat aac ggc atc atc tct atc ctc ttt gct ttg ggt ctg tac aac      1056
His Asp Asn Gly Ile Ile Ser Ile Leu Phe Ala Leu Gly Leu Tyr Asn
            340                 345                 350
```

-continued

```
ggc acc aag ccg ctg tct tcc acg acc gcg gag aat atc acc cag acc      1104
Gly Thr Lys Pro Leu Ser Ser Thr Thr Ala Glu Asn Ile Thr Gln Thr
        355                 360                 365 gat ggg ttc tca tct gcc tgg acg gtt cct ttc gcg tcg cgc atg tac      1152
Asp Gly Phe Ser Ser Ala Trp Thr Val Pro Phe Ala Ser Arg Met Tyr
    370                 375                 380 gtc gag atg atg caa tgc cag tcc gag cag gag cct ttg gtc cgt gtc      1200
Val Glu Met Met Gln Cys Gln Ser Glu Gln Glu Pro Leu Val Arg Val
385                 390                 395                 400 ttg gtt aat gat cgt gtt gtt ccg ctg cat ggc tgt ccg gtt gat gct      1248
Leu Val Asn Asp Arg Val Val Pro Leu His Gly Cys Pro Val Asp Ala
                405                 410                 415 ttg gga aga tgt acg cgg gat agc ttc gtg aag ggg ttg agc ttt gcc      1296
Leu Gly Arg Cys Thr Arg Asp Ser Phe Val Lys Gly Leu Ser Phe Ala
            420                 425                 430 aga tct ggc ggt gat tgg ggg gag tgt ttc gct tag                      1332
Arg Ser Gly Gly Asp Trp Gly Glu Cys Phe Ala
        435                 440

<210> SEQ ID NO 5
<211> LENGTH: 1515
<212> TYPE: DNA
<213> ORGANISM: Aspergillus niger
<220> FEATURE:
<221> NAME/KEY: sig_peptide
<222> LOCATION: (1)..(45)
<221> NAME/KEY: CDS
<222> LOCATION: (1)..(45)
<221> NAME/KEY: sig_peptide
<222> LOCATION: (157)..(183)
<221> NAME/KEY: mat_peptide
<222> LOCATION: (184)..(1512)
<221> NAME/KEY: CDS
<222> LOCATION: (157)..(1512)

<400> SEQUENCE: 5 atg ggt gtc tct gcc gtt cta ctt cct ttg tac ctc ctg tcc ggg          45
Met Gly Val Ser Ala Val Leu Leu Pro Leu Tyr Leu Leu Ser Gly
                -20                 -15                 -10 tatgctaatc atccctatcg gagcctgata tggaccctcc ccttccgaag gccccctgaa   105
gcttggactg tgtgggacta ttgatctgat cgctgacaat ctgtgcacag a gtc acc    162
                                                        Val Thr tcc gga ctg gca gtc ccc gcc tcg aga aat caa tcc act tgc gat acg     210
Ser Gly Leu Ala Val Pro Ala Ser Arg Asn Gln Ser Thr Cys Asp Thr
        -5                  -1  1                   5 gtc gat cag ggg tat caa tgc ttc tcg gag act tcg cat ctt tgg ggc     258
Val Asp Gln Gly Tyr Gln Cys Phe Ser Glu Thr Ser His Leu Trp Gly
10                  15                  20                  25 caa tac gcg ccg ttc ttt tct ctg gca aac aaa tcg gcc atc tcc cct     306
Gln Tyr Ala Pro Phe Phe Ser Leu Ala Asn Lys Ser Ala Ile Ser Pro
                30                  35                  40 gat gtt cct gcc gga tgc cat gtc act ttc gcc cag gtt ctc tcc cgc     354
Asp Val Pro Ala Gly Cys His Val Thr Phe Ala Gln Val Leu Ser Arg
            45                  50                  55 cat gga gca cgg tat ccg acc gac tcc aag ggc aag aaa tac tcc gct     402
His Gly Ala Arg Tyr Pro Thr Asp Ser Lys Gly Lys Lys Tyr Ser Ala
        60                  65                  70 ctc atc gag gag atc cag cag aac gcg aca acc ttc gag ggg aaa tat     450
Leu Ile Glu Glu Ile Gln Gln Asn Ala Thr Thr Phe Glu Gly Lys Tyr
    75                  80                  85 gcc ttc ctg aag aca tac aac tac agc ctg ggc gcg gat gat ctg act     498
Ala Phe Leu Lys Thr Tyr Asn Tyr Ser Leu Gly Ala Asp Asp Leu Thr
```

-continued

| | |
|---|---|
| ccc ttc gga gag cag gag ctg gtc aac tcc ggc gtc aag ttc tac cag<br>Pro Phe Gly Glu Gln Glu Leu Val Asn Ser Gly Val Lys Phe Tyr Gln<br>110                           115                    120 | 546 |
| cga tac gaa tcg ctc aca aga aac att gtc ccg ttc atc cga tcc tca<br>Arg Tyr Glu Ser Leu Thr Arg Asn Ile Val Pro Phe Ile Arg Ser Ser<br>         125                    130                  135 | 594 |
| ggc tcc agc cgc gtg att gcc tct ggc aat aaa ttc atc gag ggc ttc<br>Gly Ser Ser Arg Val Ile Ala Ser Gly Asn Lys Phe Ile Glu Gly Phe<br>140                         145                    150 | 642 |
| cag agc act aag ctg aag gat cct cgt gcc cag ccc ggc caa tcg tcg<br>Gln Ser Thr Lys Leu Lys Asp Pro Arg Ala Gln Pro Gly Gln Ser Ser<br>     155                    160                  165 | 690 |
| ccc aag atc gac gtg gtc att tca gag gcc agc aca tcc aac aac act<br>Pro Lys Ile Asp Val Val Ile Ser Glu Ala Ser Thr Ser Asn Asn Thr<br>170                      175                  180              185 | 738 |
| ctc gat ccg ggc acc tgc acc gtt ttc gaa gat agc gaa ttg gcc gat<br>Leu Asp Pro Gly Thr Cys Thr Val Phe Glu Asp Ser Glu Leu Ala Asp<br>             190                    195                  200 | 786 |
| gac atc gaa gcc aat ttc acc gcc acg ttc gtc ccc tcc att cgt caa<br>Asp Ile Glu Ala Asn Phe Thr Ala Thr Phe Val Pro Ser Ile Arg Gln<br>         205                    210                  215 | 834 |
| cgt ctg gag aac gac ttg tct ggc gtg tct ctc acg gac aca gaa gtg<br>Arg Leu Glu Asn Asp Leu Ser Gly Val Ser Leu Thr Asp Thr Glu Val<br>             220                    225                  230 | 882 |
| acc tac ctc atg gac atg tgc tcc ttc gac acc atc tcc acc agc acc<br>Thr Tyr Leu Met Asp Met Cys Ser Phe Asp Thr Ile Ser Thr Ser Thr<br>235                      240                    245 | 930 |
| gtc gac acc aag ctg tcc ccc ttc tgt gac ctg ttc acc cat gaa gaa<br>Val Asp Thr Lys Leu Ser Pro Phe Cys Asp Leu Phe Thr His Glu Glu<br>250                      255                  260              265 | 978 |
| tgg atc aac tac gac tac ctc cag tcc ctg aac aaa tac tac ggc cat<br>Trp Ile Asn Tyr Asp Tyr Leu Gln Ser Leu Asn Lys Tyr Tyr Gly His<br>             270                    275                  280 | 1026 |
| ggc gca ggt aac ccg ctc ggc ccg acc cag ggc gtc ggc tac gct aac<br>Gly Ala Gly Asn Pro Leu Gly Pro Thr Gln Gly Val Gly Tyr Ala Asn<br>         285                    290                  295 | 1074 |
| gag ctc atc gcc cgt ctc acc cac tcg cct gtc cac gat gac acc agc<br>Glu Leu Ile Ala Arg Leu Thr His Ser Pro Val His Asp Asp Thr Ser<br>             300                    305                  310 | 1122 |
| tcc aac cac aca ttg gac tcc aac ccg gct act ttc ccg ctc aac tcc<br>Ser Asn His Thr Leu Asp Ser Asn Pro Ala Thr Phe Pro Leu Asn Ser<br>         315                    320                  325 | 1170 |
| act ctc tat gcg gac ttt tcg cat gat aac ggc atc atc tct atc ctc<br>Thr Leu Tyr Ala Asp Phe Ser His Asp Asn Gly Ile Ile Ser Ile Leu<br>330                      335                  340              345 | 1218 |
| ttt gct ttg ggt ctg tac aac ggc acc aag ccg ctg tct tcc acg acc<br>Phe Ala Leu Gly Leu Tyr Asn Gly Thr Lys Pro Leu Ser Ser Thr Thr<br>             350                    355                  360 | 1266 |
| gcg gag aat atc acc cag acc gat ggg ttc tca tct gcc tgg acg gtt<br>Ala Glu Asn Ile Thr Gln Thr Asp Gly Phe Ser Ser Ala Trp Thr Val<br>         365                    370                  375 | 1314 |
| cct ttc gcg tcg cgc atg tac gtc gag atg atg caa tgc cag tcc gag<br>Pro Phe Ala Ser Arg Met Tyr Val Glu Met Met Gln Cys Gln Ser Glu<br>             380                    385                  390 | 1362 |
| cag gag cct ttg gtc cgt gtc ttg gtt aat gat cgt gtt gtt ccg ctg<br>Gln Glu Pro Leu Val Arg Val Leu Val Asn Asp Arg Val Val Pro Leu<br>         395                    400                  405 | 1410 |
| cat ggc tgt ccg gtt gat gct ttg gga aga tgt acg cgg gat agc ttc | 1458 |

-continued

```
His Gly Cys Pro Val Asp Ala Leu Gly Arg Cys Thr Arg Asp Ser Phe
410                 415                 420                 425 gtg aag ggg ttg agc ttt gcc aga tct ggc ggt gat tgg ggg gag tgt      1506
Val Lys Gly Leu Ser Phe Ala Arg Ser Gly Gly Asp Trp Gly Glu Cys
                430                 435                 440 ttc gct tag                                                          1515
Phe Ala
```

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 6
gggaattcat gggcgtctct gctgttctac tt                                  32

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 7
gggaattcct aagcaaaaca ctccgcccaa tc                                  32